US012018337B2

(12) United States Patent
Kim

(10) Patent No.: US 12,018,337 B2
(45) Date of Patent: Jun. 25, 2024

(54) NANO-VESICLE DERIVED FROM CATENIBACTERIUM BACTERIA AND USE THEREOF

(71) Applicant: MD HEALTHCARE INC., Seoul (KR)

(72) Inventor: Yoon-Keun Kim, Gyeonggi-do (KR)

(73) Assignee: MD HEALTHCARE INC., Seoul (KR)

( * ) Notice: Subject to any disclaimer, the term of this patent is extended or adjusted under 35 U.S.C. 154(b) by 980 days.

(21) Appl. No.: 16/971,044

(22) PCT Filed: Feb. 18, 2019

(86) PCT No.: PCT/KR2019/001906
§ 371 (c)(1),
(2) Date: Aug. 19, 2020

(87) PCT Pub. No.: WO2019/164197
PCT Pub. Date: Aug. 29, 2019

(65) Prior Publication Data
US 2022/0186292 A1 Jun. 16, 2022

(30) Foreign Application Priority Data

Feb. 20, 2018 (KR) .................. 10-2018-0020061
Feb. 14, 2019 (KR) .................. 10-2019-0017017

(51) Int. Cl.
*C12Q 1/689* (2018.01)
*A23L 33/00* (2016.01)
(Continued)

(52) U.S. Cl.
CPC ............ *C12Q 1/689* (2013.01); *A23L 33/135* (2016.08); *A23L 33/40* (2016.08); *A61K 35/74* (2013.01);
(Continued)

(58) Field of Classification Search
CPC .............. C12Q 1/689; C12Q 2600/158; C12Q 1/6886; A23L 33/135; A23L 33/40; A61K 35/74; A23V 2002/00; A61P 29/00
See application file for complete search history.

(56) References Cited

U.S. PATENT DOCUMENTS 9,274,109 B2 * 3/2016 Kim ..................... A61P 1/00
2012/0159658 A1 * 6/2012 Gho ..................... A61P 31/04
424/234.1
(Continued)

FOREIGN PATENT DOCUMENTS

CN 102480932 A 5/2012
KR 101940423 B1 1/2019
(Continued)

OTHER PUBLICATIONS

Ascher, Stefanie, and Christoph Reinhardt. "The gut microbiota: an emerging risk factor for cardiovascular and cerebrovascular disease." European Journal of Immunology 48.4 (Dec. 12, 2017): 564-575 (Year: 2017).*
(Continued)

Primary Examiner — Nancy J Leith
Assistant Examiner — Kyle Thomas Rega
(74) Attorney, Agent, or Firm — Riverside Law LLP

(57) ABSTRACT

The present invention relates to vesicles derived from bacteria of the genus *Catenibacterium* and a use thereof, and the inventors experimentally confirmed that the vesicles were significantly reduced in samples obtained from patients with a malignant disease such as colon cancer, pancreatic cancer, cholangiocarcinoma, ovarian cancer, bladder cancer or lymphoma, a cardiovascular disease such as myocardial infarction, atrial fibrillation, variant angina or stroke, diabetes, Parkinson's disease, and depression, compared with a normal individual, and that when vesicles isolated from the strain were administered, the secretion of inflammatory
(Continued)

mediators caused by pathogenic vesicles, such as *E. coli*-derived vesicles, was significantly inhibited. Therefore, it is expected that the vesicles derived from bacteria of the genus *Catenibacterium* according to the present invention can be effectively used for a method of diagnosing a malignant disease such as colon cancer, pancreatic cancer, cholangiocarcinoma, ovarian cancer, bladder cancer or lymphoma, a cardiovascular disease such as myocardial infarction, atrial fibrillation, variant angina pectoris or stroke, diabetes, Parkinson's disease, and depression, and for developing a composition for preventing or treating the diseases.

5 Claims, 17 Drawing Sheets
Specification includes a Sequence Listing.

(51) Int. Cl.
  *A23L 33/135* (2016.01)
  *A61K 35/74* (2015.01)
(52) U.S. Cl.
  CPC .... *A23V 2002/00* (2013.01); *C12Q 2600/158* (2013.01)

(56) References Cited

U.S. PATENT DOCUMENTS

| | | | |
|---|---|---|---|
| 2018/0256490 A1* | 9/2018 | Kim | A61K 35/745 |
| 2018/0271773 A1* | 9/2018 | Lee | A61P 17/00 |
| 2019/0350854 A1* | 11/2019 | Kwon | A61P 35/00 |

FOREIGN PATENT DOCUMENTS

| | | |
|---|---|---|
| WO | 2011027971 A2 | 3/2011 |
| WO | 2014121610 A1 | 8/2014 |
| WO | 2016086205 A2 | 6/2016 |

OTHER PUBLICATIONS

BetterHealth. "Heart Disease and Stroke." Vic.gov.au, 2012, www.betterhealth.vic.gov.au/health/conditionsandtreatments/heart-disease-and-stroke (Year: 2012).*
Kang, Chil-sung, et al. "Extracellular vesicles derived from gut microbiota, especially Akkermansia muciniphila, protect the progression of dextran sulfate sodium-induced colitis." PloS one 8.10 (2013): e76520 (Year: 2013).*
Brown, Lisa, et al. "Through the wall: extracellular vesicles in Gram-positive bacteria, mycobacteria and fungi." Nature Reviews Microbiology 13.10 (2015): 620-630 (Year: 2015).*
Kageyama, Akiko, and Yoshimi Benno. "*Catenibacterium mitsuokai* gen. nov., sp. nov., a gram-positive anaerobic bacterium isolated from human faeces." International journal of systematic and evolutionary microbiology 50.4 (2000): 1595-1599 (Year: 2000).*
Mokoena, Mduduzi Paul. "Lactic acid bacteria and their bacteriocins: classification, biosynthesis and applications against uropathogens: a mini-review." Molecules 22.8 (2017): 1255 (Year: 2017).*
Yamashita, Tomoya et al., "Gut microbiota and coronary artery disease", International Heart Journal, 2016, vol. 57 (6), pp. 1-9.
Ascher, Stefanie et al., The gut microbiota: an emerging risk factor for cardiovascular and cerebrovascular disease, European Journal of Immunology, Jan. 19, 2018, vol. 48(4), pp. 564-575.
Kelly, Tanika N. et al., "Gut microbiome associates with lifetime cardiovascular disease risk profile among bogalusa heart study participants", Circulation Research, 2016, vol. 119, pp. 956-964.
Chinese Office Action for App. No. CN201980014391.3, dated Dec. 21, 2021, 7 pages.
English translation of Chinese Office Action for App. No. CN201980014391.3, dated Dec. 21, 2021, 7 pages.

* cited by examiner

NANO-VESICLE DERIVED FROM CATENIBACTERIUM BACTERIA AND USE THEREOF

CROSS-REFERENCE TO RELATED APPLICATIONS

This application is the U.S. national phase application filed under 35 U.S.C. § 371 claiming benefit to International Patent Application No. PCT/KR2019/001906, filed on Feb. 18, 2019, which claims priority to Korean Patent Application No. 10-2018-0020061, filed Feb. 20, 2018, and Korean Patent Application No. 10-2019-0017017, filed Feb. 14, 2020, the disclosures of which are incorporated herein by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "206132-0098-00US_Sequence_Listing_v2.txt" in ASCII format. The text file containing the Sequence Listing of the present application was created on Jan. 11, 2020 and is 881 bytes in size.

TECHNICAL FIELD

The present invention relates to nanovesicles derived from bacteria of the genus *Catenibacterium* and a use thereof, and more particularly, to a method of diagnosing a malignant disease such as colon cancer, pancreatic cancer, cholangiocarcinoma, ovarian cancer, bladder cancer or lymphoma, a cardiovascular disease such as myocardial infarction, atrial fibrillation, variant angina or stroke, diabetes, Parkinson's disease, or depression using nanovesicles derived from bacteria of the genus *Catenibacterium*, and a composition for preventing, alleviating or treating the disease, which comprises the vesicle.

BACKGROUND ART

Since the beginning of the 21st century, acute infectious diseases recognized as epidemic diseases in the past have become less important, whereas chronic inflammatory diseases accompanied by immune dysfunction caused by disharmony between humans and microbiomes have changed disease patterns as main diseases that determine the quality of life and the human lifespan. As an intractable chronic disease in the 21st century, cancer, cardiovascular diseases, chronic lung diseases, metabolic diseases, and neuropsychiatric diseases have become a big problem for public health in the country as main diseases that determine the human lifespan and the quality of life. Especially, the intractable chronic diseases are characterized by chronic inflammation accompanying abnormal immune functions caused by causative factors.

It is known that the number of microorganisms coexisting in the human body has reached 100 trillion, which is 10 times more than the number of human cells, and the number of microorganism genes is more than 100 times the number of human genes. A microbiota or microbiome refers to a microbial community including bacteria, archaea and eukarya present in a given habitat.

Bacteria coexisting in our body and bacteria present in the ambient environment secrete nanometer-sized vesicles in order to exchange information on genes, low molecular compounds, proteins, and the like with other cells. The mucosa forms a physical defense membrane through which particles having a size of 200 nanometers (nm) or more cannot pass, so that bacteria coexisting in the mucosa cannot pass through the mucosa, but vesicles derived from bacteria have a size of 100 nanometers or less and are absorbed into our bodies after relatively freely passing through epithelial cells via the mucosa. Bacteria-derived vesicles that are locally secreted from bacteria are absorbed via epithelial cells of the mucous membrane to thereby induce a local inflammatory response, and the vesicles having passed through the epithelial cells are systematically absorbed via lymphatic vessels and thereby distributed in respective organs, and immune and inflammatory responses are regulated in the organs in which the vesicles are distributed. For example, vesicles derived from pathogenic gram-negative bacteria such as *Escherichia coli* locally cause colitis, and promote a systemic inflammatory response, and blood coagulation through a vascular endothelial inflammatory response when absorbed into blood vessels, and cause insulin resistance and diabetes when absorbed into insulin-acting muscle cells. On the other hand, vesicles derived from beneficial bacteria may control a disease by controlling immune dysfunction and metabolic dysfunction caused by pathogenic vesicles.

As immune responses to factors such as bacteria-derived vesicles, Th17 immune responses characterized by the secretion of the interleukin (hereinafter, IL)-17 cytokine occur, and IL-6 is secreted when exposed to bacteria-derived vesicles, thereby inducing Th17 immune responses. Inflammation caused by the Th17 immune response is characterized by neutrophil infiltration, and during the process by which inflammation occurs, tumor necrosis factor-alpha (hereinafter, TNF-α) secreted from inflammatory cells such as macrophages plays an important role. Bacteria of the genus *Catenibacterium* are anaerobic gram-positive bacteria, known to symbiotically live in the intestines. However, to date, it has not been reported that the genus *Catenibacterium* bacteria extracellularly secrete vesicles, and particularly, no cases of applying the vesicles to the diagnosis and treatment of cancer, cardiovascular diseases, metabolic diseases and neuropsychiatric disorders have been reported.

DISCLOSURE

Technical Problem

As a result of conducting earnest research to solve the above conventional problems, the inventors confirmed that a content of vesicles derived from bacteria of the genus *Catenibacterium* is significantly decreased in a sample derived from a patient with a malignant disease such as colon cancer, pancreatic cancer, cholangiocarcinoma, ovarian cancer, bladder cancer or lymphoma, a cardiovascular disease such as myocardial infarction, atrial fibrillation, variant angina pectoris or stroke, diabetes, Parkinson's disease, or depression, compared with a normal individual, through metagenomic analysis. In addition, it was confirmed that, when vesicles were isolated from *Catenibacterium mituokai* included in the genus *Catenibacterium* bacteria to treat macrophages, IL-6 and TNF-α secretion caused by pathogenic vesicles was significantly inhibited, and according to the evaluation of anticancer efficacy in mouse cancer models, when *Catenibacterium mituokai*-derived vesicles were administered, carcinogenesis was significantly inhibited. Thus, the present invention was completed.

Thus, an object of the present invention is to provide a method of providing information for diagnosis of a malignant disease such as colon cancer, pancreatic cancer, cholangiocarcinoma, ovarian cancer, bladder cancer or lymphoma, a cardiovascular disease such as myocardial infarction, atrial fibrillation, variant angina pectoris or stroke, diabetes, Parkinson's disease, or depression.

Further, another object of the present invention is to provide a composition for preventing, alleviating or treating a malignant disease such as colon cancer, pancreatic cancer, cholangiocarcinoma, ovarian cancer, bladder cancer or lymphoma, a cardiovascular disease such as myocardial infarction, atrial fibrillation, variant angina pectoris or stroke, diabetes, Parkinson's disease, or depression, comprising *Catenibacterium*-derived vesicles as an active ingredient.

However, a technical problem to be achieved by the present invention is not limited to the aforementioned problems, and the other problems that are not mentioned may be clearly understood by a person skilled in the art from the following description.

Technical Solution

To achieve the object of the present invention as described above, the present invention provides a method of providing information for diagnosing colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression, the method comprising the following steps:
(a) extracting DNAs from extracellular vesicles isolated from samples of a normal individual and a subject;
(b) performing polymerase chain reaction (PCR) on the extracted DNA using a pair of primers prepared based on a gene sequence present in 16S rDNA to obtain each PCR product; and
(c) classifying a case in which a content of extracellular vesicles derived from bacteria of the genus *Catenibacterium* is lower than that of the normal individual sample, as colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression, through quantitative analysis of the PCR product.

In addition, the present invention provides a method of diagnosing colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression, the method comprising the following steps:
(a) extracting DNAs from extracellular vesicles isolated from samples of a normal individual and a subject;
(b) performing polymerase chain reaction (PCR) on the extracted DNA using a pair of primers prepared based on a gene sequence present in 16S rDNA to obtain each PCR product; and
(c) classifying a case in which a content of extracellular vesicles derived from bacteria of the genus *Catenibacterium* is lower than that of the normal individual sample, as colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression, through quantitative analysis of the PCR product.

As an exemplary embodiment of the present invention, the sample in Step (a) may be blood, urine, or stool.

As another embodiment of the present invention, the primer pair in Step (b) may be primers of SEQ ID Nos. 1 and 2.

Further, the present invention provides a pharmaceutical composition for preventing or treating colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression, comprising vesicles derived from bacteria of the genus *Catenibacterium* as an active ingredient.

Further, the present invention provides a food composition for preventing or alleviating colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression, comprising vesicles derived from bacteria of the genus *Catenibacterium* as an active ingredient.

Further, the present invention provides a method of preventing or treating colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression, the method comprising a step of administering a pharmaceutical composition comprising vesicles derived from bacteria of the genus *Catenibacterium* as an active ingredient to a subject.

Further, the present invention provides a use of vesicles derived from bacteria of the genus *Catenibacterium* for preventing or treating colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression.

In one embodiment of the present invention, the vesicles may have an average diameter of 10 to 200 nm.

In another embodiment of the present invention, the vesicles may be secreted naturally or artificially from bacteria of the genus *Catenibacterium*.

In another embodiment of the present invention, the vesicles derived from bacteria of the genus *Catenibacterium* may be vesicles derived from *Catenibacterium* mituokai.

Advantageous Effects

The inventors confirmed that intestinal bacteria are not absorbed into the body through epithelial cells, but bacteria-derived vesicles are absorbed, systemically distributed and then excreted out of the body through the kidneys, liver and lungs, and by metagenomic analysis for vesicles derived from bacteria present in patients' blood, urine or stool, also confirmed that vesicles derived from bacteria of the genus *Catenibacterium*, which are present in blood, urine or stool of patients with a malignant disease such as colon cancer, pancreatic cancer, cholangiocarcinoma, ovarian cancer, bladder cancer or lymphoma, a cardiovascular disease such as myocardial infarction, atrial fibrillation, variant angina pectoris or stroke, diabetes, Parkinson's disease, and depression significantly decrease, compared with a normal individual. In addition, when *Catenibacterium* mituokai, which is one species of bacteria of the genus *Catenibacterium*, was cultured in vitro to isolate vesicles, and then the vesicles were administered to inflammatory cells in vitro, it was confirmed that the secretion of inflammation mediators, mediated by pathogenic vesicles was significantly inhibited. Therefore, it is expected that the vesicles derived from bacteria of the genus *Catenibacterium* according to the present invention can be effectively used for a method of diagnosing a malignant disease such as colon cancer, pancreatic cancer, cholangiocarcinoma, ovarian cancer, bladder cancer or lymphoma, a cardiovascular disease such as myocardial infarction, atrial fibrillation, variant angina pectoris or stroke, diabetes, Parkinson's disease, and depression, and a composition for preventing, alleviating or treating the diseases.

DESCRIPTION OF DRAWINGS

FIGS. 5A and 5B are result of comparing the distribution of vesicles derived from bacteria of the genus *Catenibacterium* after metagenomic analysis of bacteria-derived vesicles present in an ovarian cancer patient and a normal individual, in which FIG. 5A is a result obtained with a blood sample, and FIG. 5B is a result obtained with a urine sample.

BEST MODES

Figure 1A:
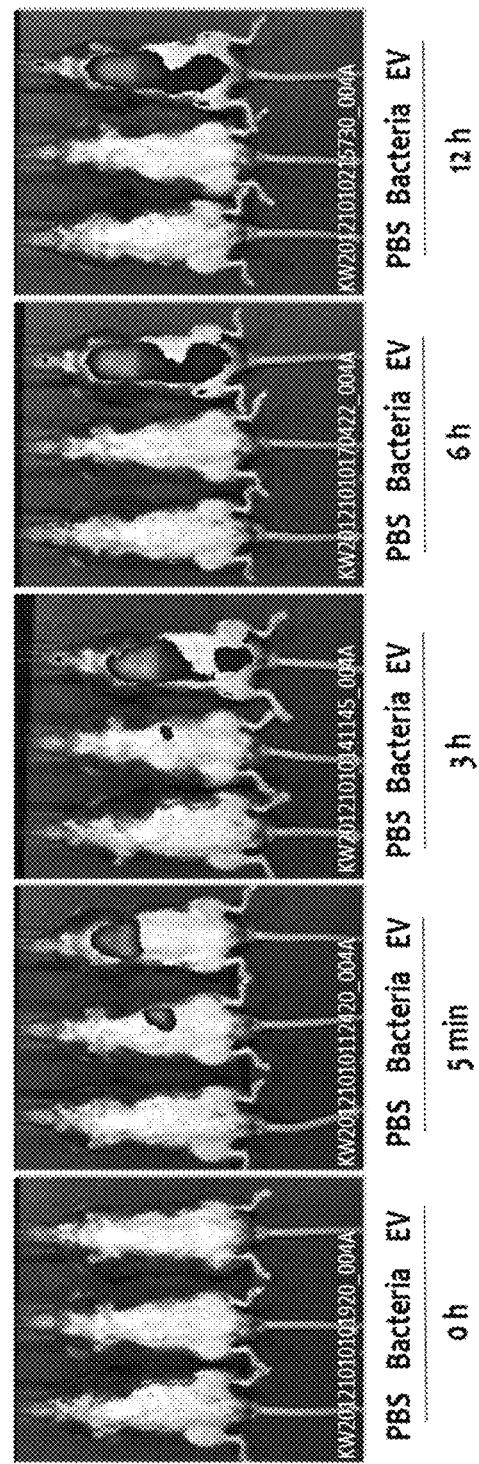
FIG. 1A is a series of photographs capturing distribution patterns of bacteria and bacteria-derived vesicles (EV) by time after the bacteria and the vesicles derived from bacteria were orally administered to mice.

The present invention relates to vesicles derived from bacteria of the genus *Catenibacterium* and a use thereof.

In the present invention, a significant decrease in vesicles derived from bacteria of the genus *Catenibacterium* in a clinical sample obtained from a patient with cancer, a cardiovascular disease, a metabolic disease, and a neuropsychiatric disease, compared with a normal individual, was confirmed through metagenomic analysis, and thus the disease can be diagnosed. In addition, as a result of isolating vesicles from *Catenibacterium mituokai* and analyzing their characteristics, it was confirmed that the vesicles can be used for a composition for preventing or treating a malignant disease, a cardiovascular disease, a metabolic disease and a neuropsychiatric disease.

Thus, the present invention provides a method of providing information for diagnosing colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression, the method comprising the following steps:

(a) extracting DNAs from extracellular vesicles isolated from samples of a normal individual and a subject;

(b) performing polymerase chain reaction (PCR) on the extracted DNA using a pair of primers prepared based on a gene sequence present in 16S rDNA to obtain each PCR product; and (c) classifying a case in which a content of extracellular vesicles derived from bacteria of the genus *Catenibacterium* is lower than that of the normal individual sample, as colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, or depression, through quantitative analysis of the PCR product.

The term "diagnosis" as used herein refers to determination of a condition of a disease of a patient over all aspects, in a broad sense. The contents of the determination are the disease entity, the etiology, the pathogenesis, the severity, the detailed aspects of a disease, the presence and absence of complications, the prognosis, and the like. The diagnosis in the present invention means determining whether cancer, an inflammatory disease, a cardiovascular disease, a metabolic disease, and/or a neuropsychiatric disease occur, the level of the disease, and the like.

The term "nanovesicle" or "vesicle" as used herein refers to a structure consisting of a nano-sized membrane secreted from various bacteria. Vesicles derived from gram-negative bacteria or outer membrane vesicles (OMVs) have endotoxins (lipopolysaccharides), toxic protein, bacterial DNA and RNA, and vesicles derived from gram-positive bacteria also have peptidoglycan and lipoteichoic acid which are cell wall components of bacteria in addition to proteins and nucleic acids. In the present invention, nanovesicles or vesicles are secreted naturally from bacteria of the genus *Catenibacterium* or produced artificially, are in the form of a sphere, and have an average diameter of 10 to 200 nm.

The vesicles may be isolated from a culturing solution comprising bacteria of the genus *Catenibacterium* by using one or more methods selected from the group consisting of centrifugation, ultra-high speed centrifugation, high pressure treatment, extrusion, sonication, cell lysis, homogenization, freezing-thawing, electroporation, mechanical decomposition, chemical treatment, filtration by a filter, gel filtration chromatography, free-flow electrophoresis, and capillary electrophoresis. Further, a process such as washing for removing impurities and concentration of obtained vesicles may be further included.

The term "metagenome" as used herein also refers to a microbiome, and refers to a total of genomes including all viruses, bacteria, fungi, and the like in an isolated region such as soil and an animal's intestines, and is typically used as a concept of genomes explaining identification of a large number of microorganisms at one time by using a sequence analyzer in order to analyze uncultivated microorganisms. In particular, the metagenome does not refer to a genome of one species, but refers to a kind of mixed genome as a genome of all species of one environmental unit. The metagenome is, when one species is defined in the development process of omics biology, a term derived from the viewpoint of making a complete species is made by various species interacting with each other as well as one kind of functionally existing species. Technically, the metagenome is an object of a technique to identify all species in one environment and investigate interactions and metabolism by analyzing all DNAs and RNAs regardless of species using a rapid sequence analysis method.

In the present invention, the sample derived from a subject may be blood, urine, or stool, but is not limited thereto.

Another aspect of the present invention provides a composition for preventing, treating or alleviating a malignant disease such as colon cancer, pancreatic cancer, cholangiocarcinoma, ovarian cancer, bladder cancer or lymphoma, a cardiovascular disease such as myocardial infarction, atrial fibrillation, variant angina or stroke, diabetes, Parkinson's disease, and depression, which comprises vesicles derived from bacteria of the genus *Catenibacterium* as an active ingredient. The composition includes a food composition and a pharmaceutical composition, and in the present invention, the food composition includes a health functional food composition. The composition of the present invention may be a formulation of an oral spray or inhalant.

The term "prevention" as used herein refers to all actions that suppress cancer, an inflammatory disease, a cardiovascular disease, a metabolic disease, and/or a neuropsychiatric disease or delay the onset thereof via administration of the composition according to the present invention.

The term "treatment" as used herein refers to all actions that alleviate or beneficially change symptoms of cancer, an inflammatory disease, a cardiovascular disease, a metabolic disease, and/or a neuropsychiatric disease via administration of composition according to the present invention.

The term "alleviation" used as used herein refers to all actions that at least reduce a parameter associated with a condition to be treated, for example, the degree of symptoms.

The pharmaceutical composition of the present invention may include a pharmaceutically acceptable carrier. The pharmaceutically acceptable carrier is typically used in formulation, and includes saline, sterile water, Ringer's solution, buffered saline, cyclodextrin, a dextrose solution, a maltodextrin solution, glycerol, ethanol, liposomes, and the like, but is not limited thereto, and may further include other typical additives such as an antioxidant and a buffer, if necessary. Further, the composition may be formulated into an injectable formulation, such as an aqueous solution, a suspension, and an emulsion, a pill, a capsule, a granule, or a tablet by additionally adding a diluent, a dispersant, a surfactant, a binder, a lubricant, and the like. With regard to suitable pharmaceutically acceptable carriers and formulations, the composition may be preferably formulated according to each ingredient by using the method disclosed in the Remington's literature. The pharmaceutical composition of the present invention is not particularly limited in formulation, but may be formulated into an injection, an inhalant, an external preparation for skin, an oral ingestion, or the like.

The pharmaceutical composition of the present invention may be administered orally or parenterally (e.g., intravenously, subcutaneously, intradermally, intranasally or intratracheally) according to a desired method, and a dose may vary according to the condition and body weight of a patient, the severity of a disease, a drug formulation, an administration route, and duration, but may be suitably selected by those of ordinary skill in the art.

The pharmaceutical composition according to the present invention is administered in a pharmaceutically effective amount. In the present invention, the pharmaceutically effective amount refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields. The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

Specifically, an effective amount of the pharmaceutical composition according to the present invention may vary according to a patient's age, gender and body weight, and generally, the pharmaceutical composition may be administered at 0.001 to 150 mg, and preferably, 0.01 to 100 mg per kg of body weight daily or every two days, or 1 to 3 times daily. However, as the dose may be increased or decreased by an administration route, the severity of obesity, gender, a body weight or an age, the above-mentioned dose does not limit the scope of the present invention in any way.

The food composition of the present invention includes a health functional food composition. The food composition according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range.

Other ingredients are not particularly limited, except that the food composition of the present invention contains the active ingredient as an essential ingredient at the indicated ratio, and the food composition of the present invention may contain various flavorants, natural carbohydrates, and the like, like a typical beverage, as an additional ingredient. Examples of the above-described natural carbohydrate include common sugars such as monosaccharides, for example, glucose, fructose and the like; disaccharides, for example, maltose, sucrose and the like; and polysaccharides, for example, dextrin, cyclodextrin and the like, and sugar alcohols such as xylitol, sorbitol, and erythritol. As the flavorant other than those described above, a natural flavorant (thaumatin, *stevia* extract, for example, rebaudioside A, glycyrrhizin and the like), and a synthetic flavorant (saccharin, aspartame and the like) may be advantageously used. The proportion of the natural carbohydrate may be appropriately determined by the choice of those of ordinary skill in the art.

The food composition of the present invention may contain various nutrients, vitamins, minerals (electrolytes), flavoring agents such as synthetic flavoring agents and natural flavoring agents, colorants and fillers (cheese, chocolate, and the like), pectic acid and salts thereof, alginic acid and salts thereof, organic acids, protective colloid thickeners, pH adjusting agents, stabilizers, preservatives, glycerin, alcohols, carbonating agents used in a carbonated beverage, or the like, in addition to the additives. These ingredients may be used either alone or in combinations thereof. The ratio of these additives may also be appropriately selected by those of ordinary skill in the art.

In one embodiment of the present invention, as a result of orally administering bacteria and bacteria-derived vesicles to mice and observing in vivo absorption, distribution, and excretion patterns of the bacteria and the vesicles, it was confirmed that, while the bacteria were not absorbed via the intestinal mucous membrane, the bacteria-derived vesicles were absorbed within 5 minutes after administration and systemically distributed, and excreted via the kidneys, liver, and the like (see Example 1).

In another embodiment of the present invention, a bacterial metagenomic analysis was performed by using vesicles isolated from the blood, urine, or stool of normal individuals who were matched in age and sex with patients with colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, and depression. As a result, it was confirmed that vesicles derived from bacteria of the genus *Catenibacterium* were significantly decreased in clinical samples of patients with colon cancer, pancreatic cancer, cholangiocarcinoma, ovarian cancer, bladder cancer, lymphoma, myocardial infarction, atrial fibrillation, variant angina pectoris, stroke, diabetes, Parkinson's disease, and depression as compared to samples of normal individuals (see Examples 3 to 15).

In another embodiment of the present invention, *Catenibacterium mituokai* was cultured to evaluate whether vesicles secreted therefrom have immunomodulatory and anti-inflammatory effects, and it was confirmed that IL-6 and TNF-α secretion caused by *Escherichia coli* vesicles (*E. coli* EVs) are effectively inhibited by *Catenibacterium mituokai*-derived vesicles through evaluation of the secretion of inflammatory mediators by treating *E. coli* EVs, which are an inflammatory disease causative factor, following treatment of macrophages with various concentrations of *Catenibacterium mituokai*-derived vesicles (refer to Example 15).

Hereinafter, preferred Examples for helping the understanding of the present invention will be suggested. However, the following Examples are provided only to more easily understand the present invention, and the contents of the present invention are not limited by the following Examples.

Modes of the Invention

EXAMPLES

Example 1. Analysis of In Vivo Absorption, Distribution, and Excretion Patterns of Intestinal Bacteria and Vesicles Derived from Bacteria In order to evaluate whether intestinal bacteria and bacteria-derived vesicles were systemically absorbed through the gastrointestinal tract, an experiment was performed with the following method. First, a dose of 50 μg of each of fluorescence-labeled intestinal bacteria and intestinal bacteria-derived vesicles was administered through the gastrointestinal tract to the stomach of a mouse, and fluorescence was measured after 0 minute, 5 minutes, 3 hours, 6 hours, and 12 hours. As a result of observing the entire image of the mouse, as illustrated in FIG. 1A, the bacteria were not systemically absorbed, but the vesicles derived from bacteria were systemically absorbed 5 minutes after administration, and fluorescence was strongly observed in the bladder 3 hours after administration, so that it could be seen that the vesicles were excreted to the urinary tract. Further, it could be seen that the vesicles were present in the body until 12 hours after administration (see FIG. 1A).

Figure 1B:
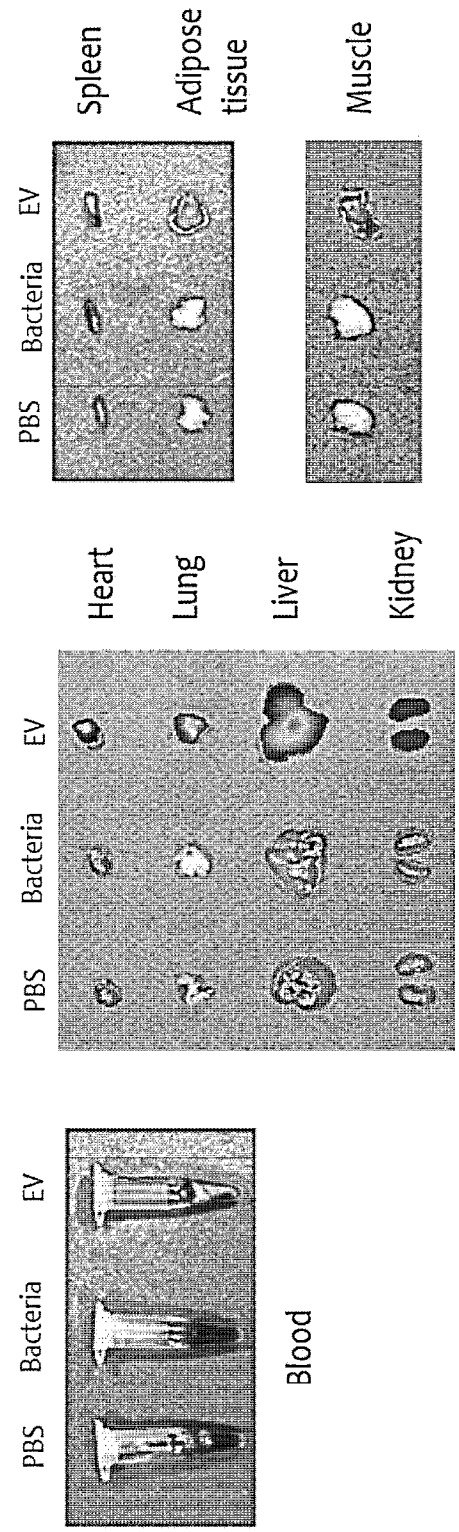
FIG. 1B is a result of evaluating the in vivo distribution patterns of the bacteria and the vesicles by harvesting blood, kidneys, liver, and various organs at 12 hours after orally administering the bacteria and the vesicles.

In order to evaluate the pattern in which the intestinal bacteria and the vesicles derived from the intestinal bacteria infiltrated into various organs after they were systemically absorbed, 50 μg of bacteria and vesicles derived from bacteria labeled with fluorescence were administered in the same manner as described above, and then the blood, heart, lungs, liver, kidneys, spleen, fat, and muscle were collected 12 hours after administration. As a result of observing fluorescence in the collected tissues, as illustrated in FIG. 1B, it could be seen that the vesicles derived from bacteria were distributed in the blood, heart, lungs, liver, spleen, fat, muscle, and kidneys but the bacteria were not absorbed (see FIG. 1B).

Example 2. Metagenomic Analysis of Vesicles Derived from Bacteria in Clinical Sample After clinical samples such as blood, urine, stool, and the like was first put into a 10-ml tube and suspended matter was allowed to settle by a centrifuge (3,500×g, 10 min, 4° C.), only the supernatant was transferred to a new 10-ml tube. After bacteria and impurities were removed by using a 0.22-μm filter, they were transferred to a Centriprep tube (centrifugal filters 50 kD) and centrifuged at 1,500×g and 4° C. for 15 minutes, materials smaller than 50 kD were discarded, and the residue was concentrated to 10 ml. After bacteria and impurities were removed once again by using a 0.22-μm filter, the supernatant was discarded by using a ultra-high speed centrifugation at 150,000×g and 4° C. for 3 hours with a Type 90Ti rotor, and an aggregated pellet was dissolved in physiological saline (PBS).

Internal DNA was extracted out of the lipid by boiling 100 μl of the vesicles isolated by the above method at 100° C., and then cooled on ice for 5 minutes. And then, in order to remove the remaining suspended matter, the DNA was centrifuged at 10,000×g and 4° C. for 30 minutes, and only the supernatant was collected. And, the amount of DNA was quantified by using Nanodrop. Thereafter, in order to confirm whether the DNA derived from bacteria was present in the extracted DNA, PCR was performed with 16s rDNA primers shown in the following Table 1 and it was confirmed that genes derived from bacteria were present in the extracted genes.

TABLE 1

| primer | | Sequence | SEQ ID No. |
|---|---|---|---|
| 16S rDNA | 16S_V3_F | 5'-TCGTCGGCAGCGTCAGATGTGTATAAGAGACAGCCTACGGGNGGCWGCAG-3' | 1 |
| | 16S_V4_R | 5'-GTCTCGTGGGCTCGGAGATGTGTATAAGAGACAGGACTACHVGGGTATCTAATCC | 2 |

The DNA extracted by the above method was amplified using the 16S rDNA primers, and then sequencing was performed (Illumina MiSeq sequencer), the results were output as a standard flowgram format (SFF) file, the SFF file was converted into a sequence file (.fasta) and a nucleotide quality score file using GS FLX software (v2.9), and then the reliability estimation for the reads was confirmed, and a portion in which the window (20 bps) average base call accuracy was less than 99% (Phred score<20) was removed. For the OTU (operational taxonomy unit) analysis, clustering was performed according to sequence similarity by using UCLUST and USEARCH, the genus, family, order, class, and phylum were clustered based on 94%, 90%, 85%, 80%, and 75% sequence similarity, respectively, classification was performed at the phylum, class, order, family, and genus levels of each OUT, and bacteria having a sequence similarity of 97% or more at the genus level were profiled by using the 16S RNA sequence database (108,453 sequences) of BLASTN and GreenGenes (QIIME).

Figure 2:
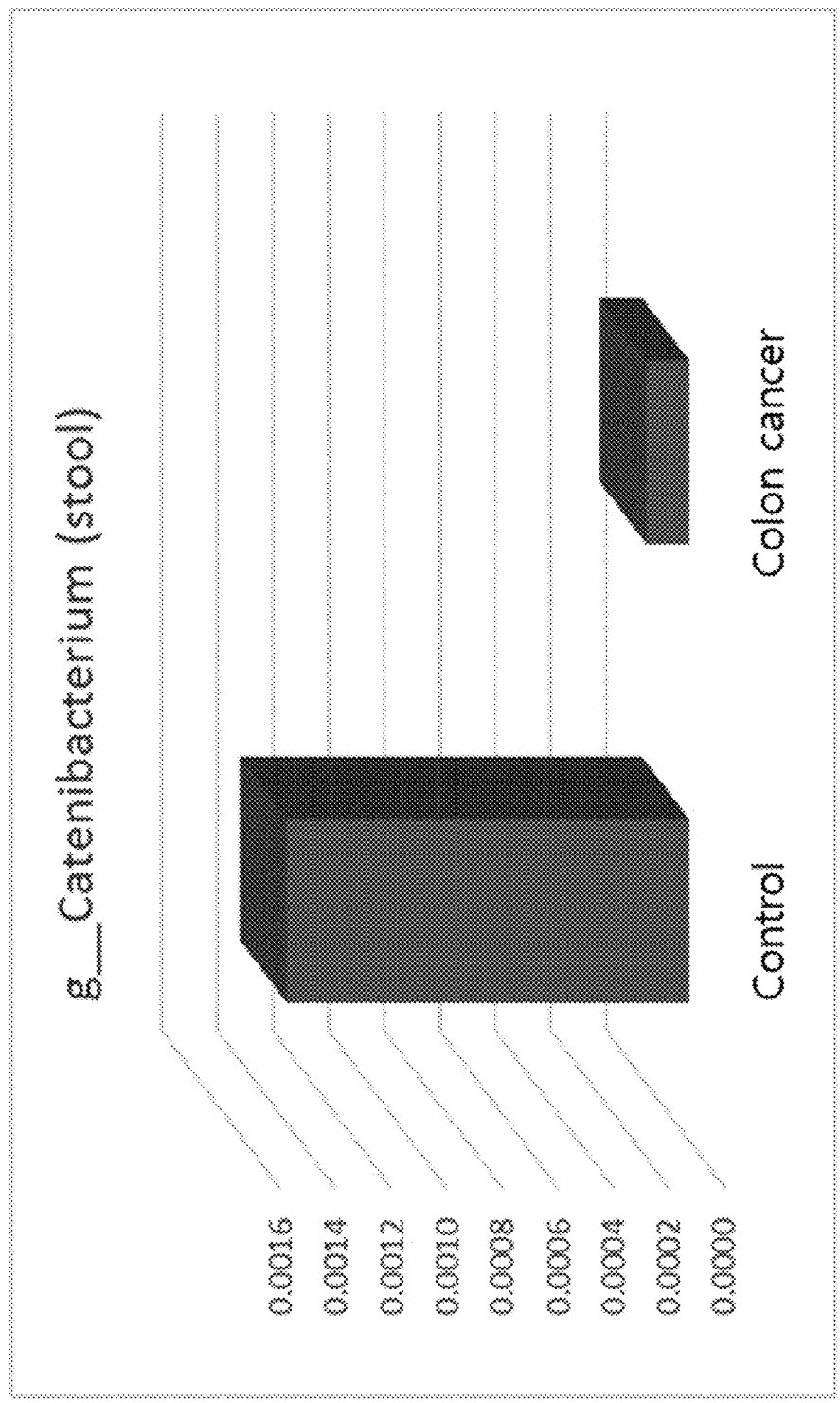
FIG. 2 is a result of comparing the distributions of vesicles derived from bacteria of the genus *Catenibacterium* after metagenomic analysis of bacteria-derived vesicles present in the stool of colon cancer patients and a normal individual.

Example 3. Metagenomic Analysis of Bacteria-Derived Vesicles in Stool of Patient with Colon Cancer After a metagenomic analysis was performed using the method of Example 2 on the stool from 38 patients with colon cancer, and 38 normal individuals who were matched in age and sex by extracting genes from vesicles present in the stool, the distribution of vesicles derived from bacteria of the genus *Catenibacterium* was evaluated. As a result, it was confirmed that vesicles derived from bacteria of the genus *Catenibacterium* were significantly decreased in the stool from the patients with colon cancer as compared to the stool from the normal individuals (see Table 2 and FIG. 2).

TABLE 2

| Stool | Control | | Colon cancer | | t-test | |
|---|---|---|---|---|---|---|
| Taxon | Mean | SD | Mean | SD | p-value | Ratio |
| g_Catenibacterium | 0.0014 | 0.0047 | 0.0002 | 0.0004 | <0.0001 | 0.11 |

Figure 3:
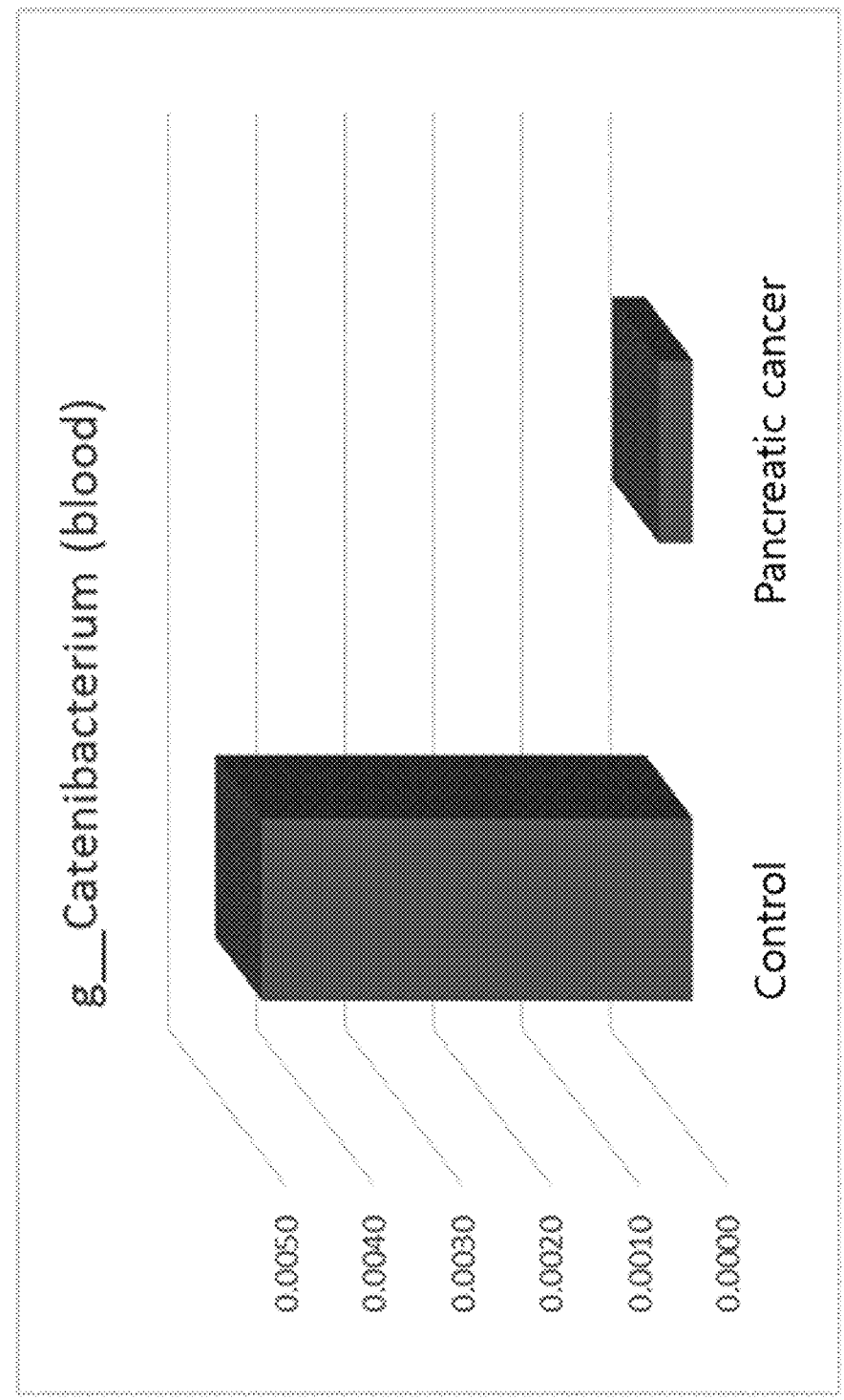
FIG. 3 is a result of comparing the distributions of vesicles derived from bacteria of the genus *Catenibacterium* after metagenomic analysis of bacteria-derived vesicles present in the blood of pancreatic cancer patients and a normal individual.

Example 4. Metagenomic Analysis of Bacteria-Derived Vesicles in Blood of Patient with Pancreatic Cancer After a metagenomic analysis was performed using the method of Example 2 on the blood from 291 patients with pancreatic cancer, and 291 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with pancreatic cancer as compared to the blood from the normal individuals (see Table 3 and FIG. 3).

TABLE 3

| Blood | Control | | Pancreatic cancer | | t-test | |
|---|---|---|---|---|---|---|
| Taxon | Mean | SD | Mean | SD | p-value | Ratio |
| g_Catenibacterium | 0.0049 | 0.0143 | 0.0004 | 0.0012 | <0.0001 | 0.08 |

Figure 4:
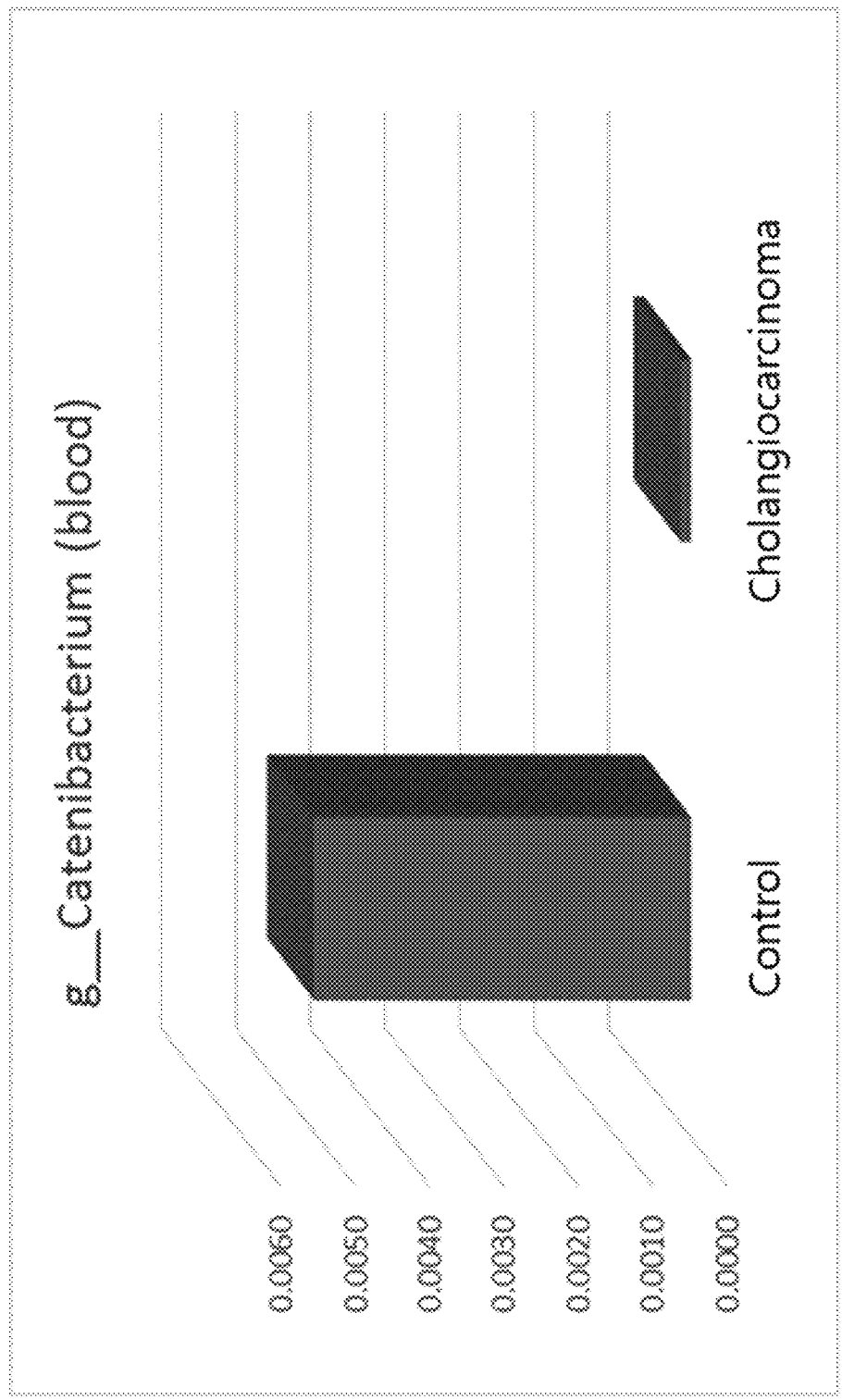
FIG. 4 is a result of comparing the distributions of vesicles derived from bacteria of the genus *Catenibacterium* after metagenomic analysis of bacteria-derived vesicles present in the blood of cholangiocarcinoma patients and a normal individual.

Example 5. Metagenomic Analysis of Bacteria-Derived Vesicles in Blood of Patient with Cholangiocarcinoma After a metagenomic analysis was performed using the method of Example 2 on the blood from 121 patients with cholangiocarcinoma, and 131 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with cholangiocarcinoma as compared to the blood from the normal individuals (see Table 4 and FIG. 4).

TABLE 4

| Blood | Control | | Cholangiocarcinoma | | t-test | |
|---|---|---|---|---|---|---|
| Taxon | Mean | SD | Mean | SD | p-value | Ratio |
| g_Catenibacterium | 0.0051 | 0.0147 | 0.0001 | 0.0010 | <0.0001 | 0.03 |

Figure 5A:
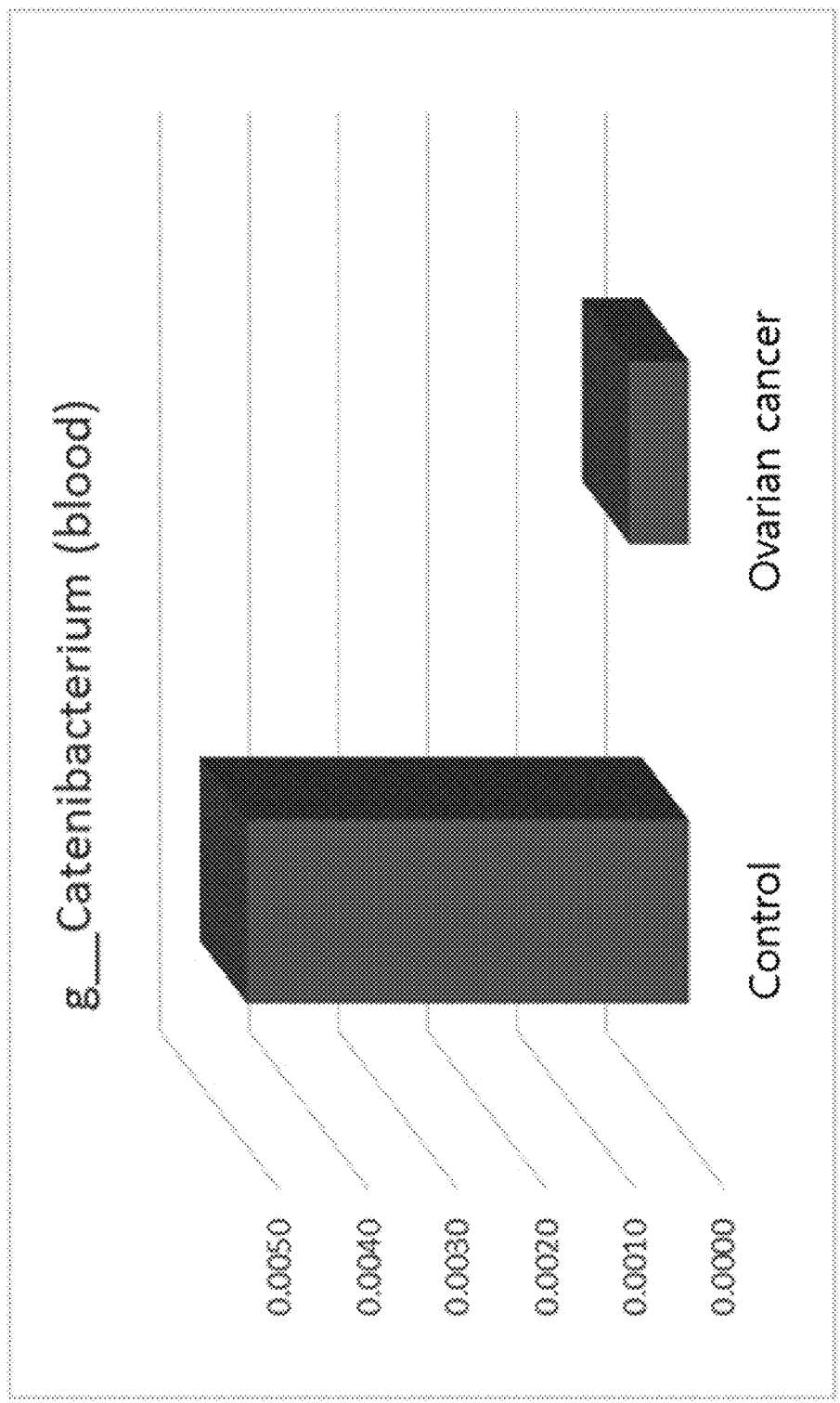

Example 6. Metagenomic Analysis of Bacteria-Derived Vesicles in Blood and Urine of Patient with Ovarian Cancer After a metagenomic analysis was performed using the method of Example 2 on the blood from 126 patients with ovarian cancer, and 131 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with ovarian cancer as compared to the blood from the normal individuals (see Table 5 and FIG. 5a).

TABLE 5

| Blood | Control | | Ovarian cancer | | t-test | |
|---|---|---|---|---|---|---|
| Taxon | Mean | SD | Mean | SD | p-value | Ratio |
| g_Catenibacterium | 0.0050 | 0.0105 | 0.0007 | 0.0015 | <0.0001 | 0.13 |

Figure 5B:
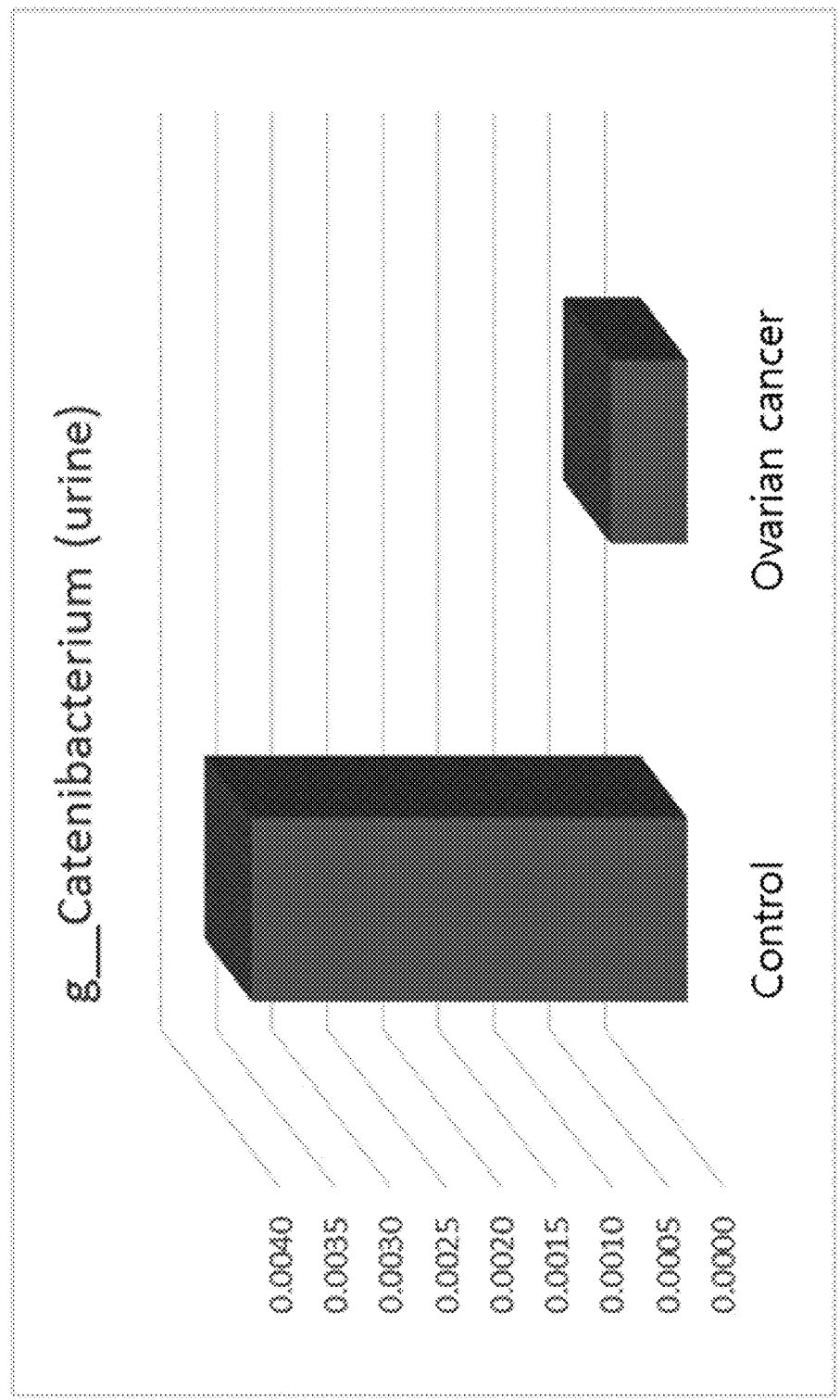

In addition, after a metagenomic analysis was performed using the method of Example 2 on the urine from 136 patients with ovarian cancer, and 136 normal individuals who were matched in age and sex by extracting genes from vesicles present in the urine, the distribution of vesicles derived from bacteria of the genus *Catenibacterium* was evaluated. As a result, it was confirmed that vesicles derived from bacteria of the genus *Catenibacterium* were significantly decreased in the urine from the patients with ovarian cancer as compared to the urine from the normal individuals (see Table 6 and FIG. 5b).

TABLE 6

| Urine | Control | | Ovarian cancer | | t-test | |
|---|---|---|---|---|---|---|
| Taxon | Mean | SD | Mean | SD | p-value | Ratio |
| g_Catenibacterium | 0.0039 | 0.0099 | 0.0007 | 0.0017 | 0.0002 | 0.18 |

Figure 6:
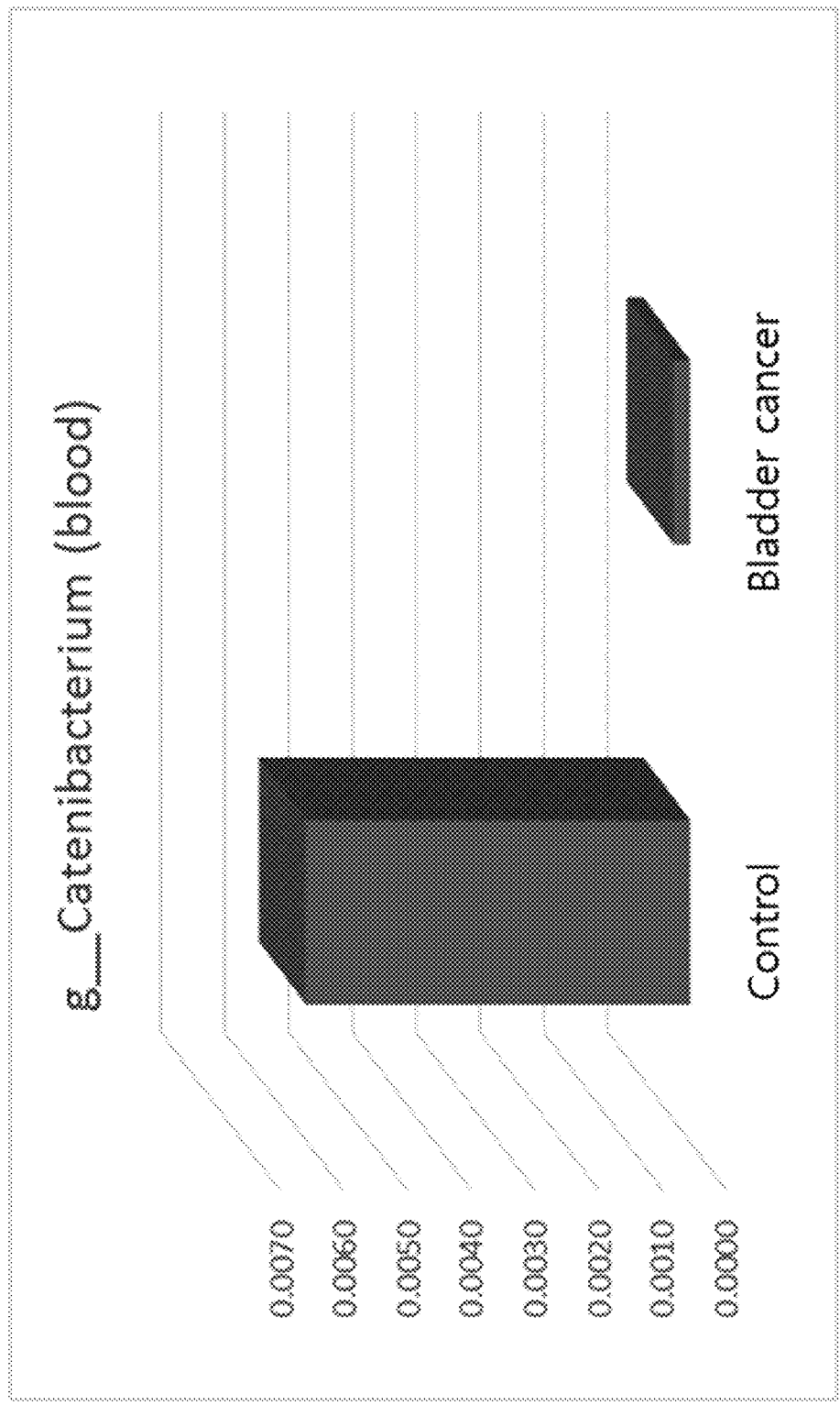
FIG. 6 is a result of comparing the distributions of vesicles derived from bacteria of the genus *Catenibacterium* after metagenomic analysis of bacteria-derived vesicles present in the blood of bladder cancer patients and a normal individual.

Example 7. Metagenomic Analysis of Bacteria-Derived Vesicles in Blood of Patient with Bladder Cancer After a metagenomic analysis was performed using the method of Example 2 on the blood from 96 patients with bladder cancer, and 184 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with bladder cancer as compared to the blood from the normal individuals (see Table 7 and FIG. 6).

TABLE 7

| Blood | Control | | Bladder cancer | | t-test | |
|---|---|---|---|---|---|---|
| Taxon | Mean | SD | Mean | SD | p-value | Ratio |
| g_Catenibacterium | 0.0060 | 0.0138 | 0.0003 | 0.0003 | <0.0001 | 0.04 |

Figure 7:
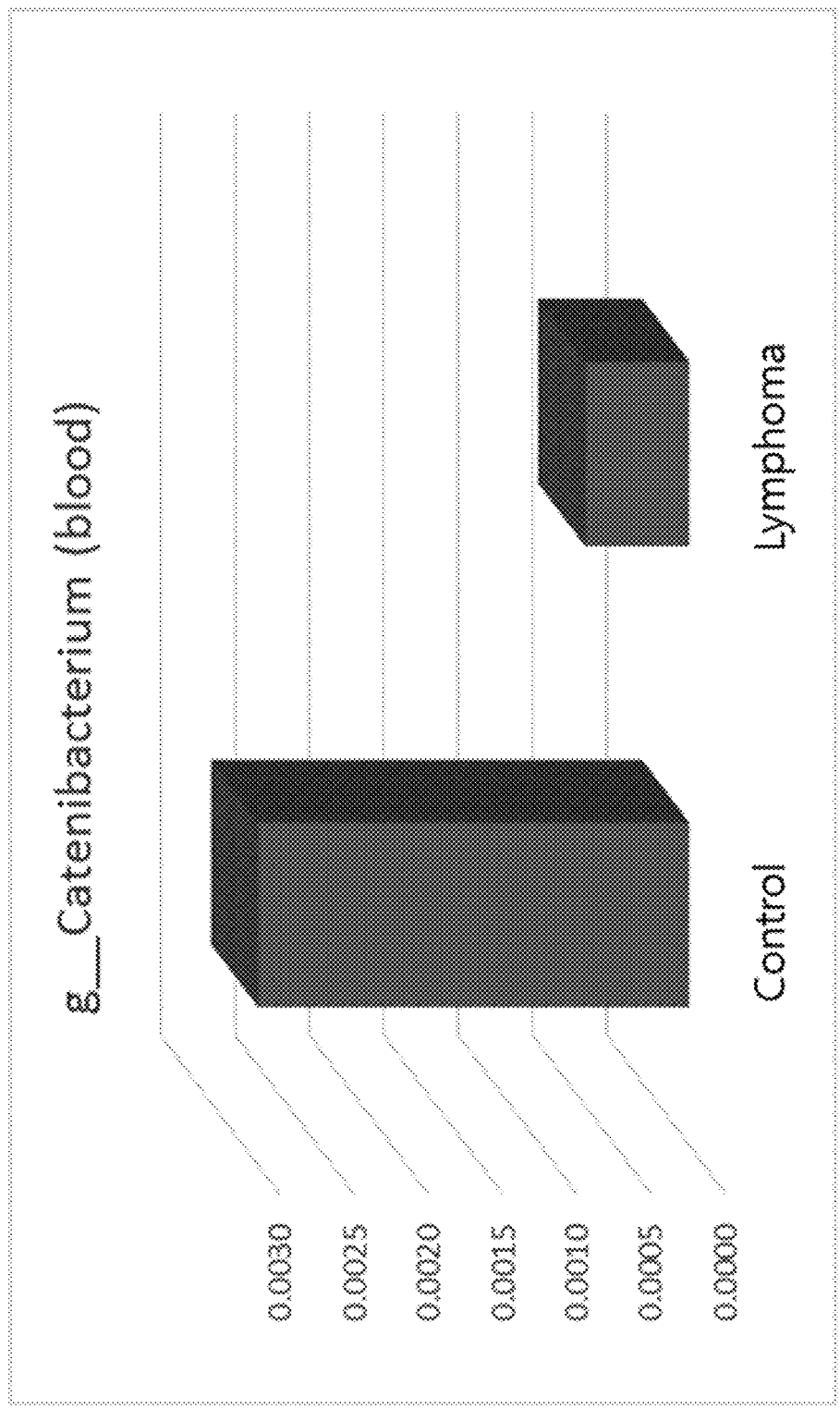
FIG. 7 is a result of comparing the distributions of vesicles derived from bacteria of the genus *Catenibacterium* after metagenomic analysis of bacteria-derived vesicles present in the blood of lymphoma patients and a normal individual.

Example 8. Metagenomic Analysis of Bacteria-Derived Vesicles in Blood of Patient with Lymphoma After a metagenomic analysis was performed using the method of Example 2 on the blood from 63 patients with lymphoma, and 53 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with lymphoma as compared to the blood from the normal individuals (see Table 8 and FIG. 7).

TABLE 8

| Blood | Control | | Lymphoma | | t-test | |
|---|---|---|---|---|---|---|
| Taxon | Mean | SD | Mean | SD | p-value | Ratio |
| g_Catenibacterium | 0.0029 | 0.0089 | 0.0007 | 0.0017 | 0.04 | 0.24 |

Figure 8:
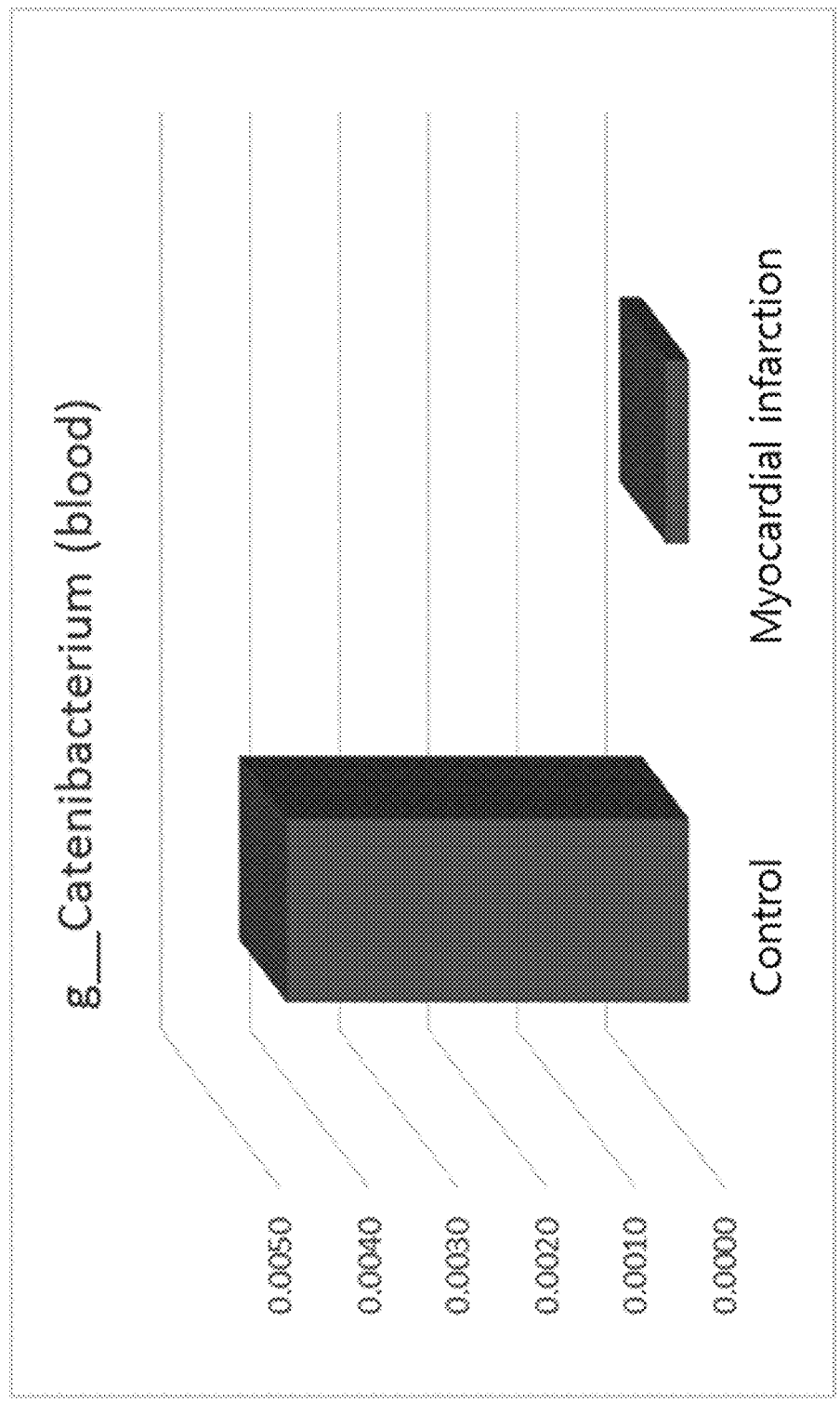
FIG. 8 is a result of comparing the distributions of vesicles derived from bacteria of the genus *Catenibacterium* after metagenomic analysis of bacteria-derived vesicles present in the blood of myocardial infarction patients and a normal individual.

Example 9. Metagenomic Analysis of Bacteria-Derived Vesicles in Blood of Patient with Myocardial Infarction After a metagenomic analysis was performed using the method of Example 2 on the blood from 57 patients with myocardial infarction, and 163 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with myocardial infarction as compared to the blood from the normal individuals (see Table 9 and FIG. 8).

TABLE 9

| Blood | Control | | Myocardial infarction | | t-test | |
|---|---|---|---|---|---|---|
| Taxon | Mean | SD | Mean | SD | p-value | Ratio |
| g_Catenibacterium | 0.0045 | 0.0104 | 0.0003 | 0.0011 | <0.0001 | 0.06 |

Figure 9:
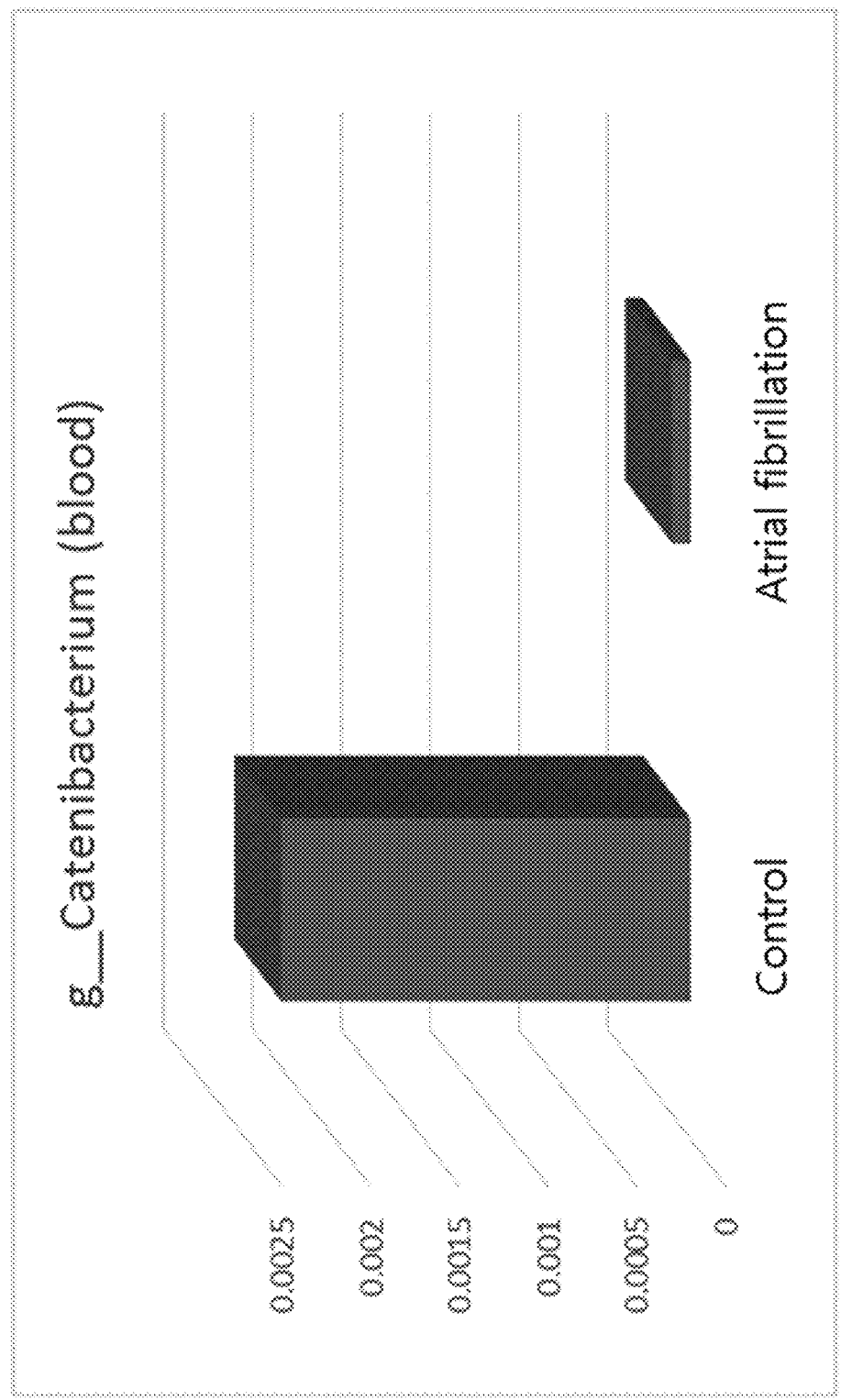
FIG. 9 is a result of comparing the distributions of vesicles derived from bacteria of the genus *Catenibacterium* after metagenomic analysis of bacteria-derived vesicles present in the blood of atrial fibrillation patients and a normal individual.

Example 10. Metagenomic Analysis of Bacteria-Derived Vesicles in Blood of Patient with Atrial Fibrillation After a metagenomic analysis was performed using the method of Example 2 on the blood from 32 patients with atrial fibrillation, and 32 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with atrial fibrillation as compared to the blood from the normal individuals (see Table 10 and FIG. 9).

TABLE 10

| Blood | Control | | Atrial fibrillation | | t-test | |
|---|---|---|---|---|---|---|
| Taxon | Mean | SD | Mean | SD | p-value | Ratio |
| g_Catenibacterium | 0.0023 | 0.0055 | 0.0001 | 0.0003 | 0.002 | 0.04 |

Figure 10:
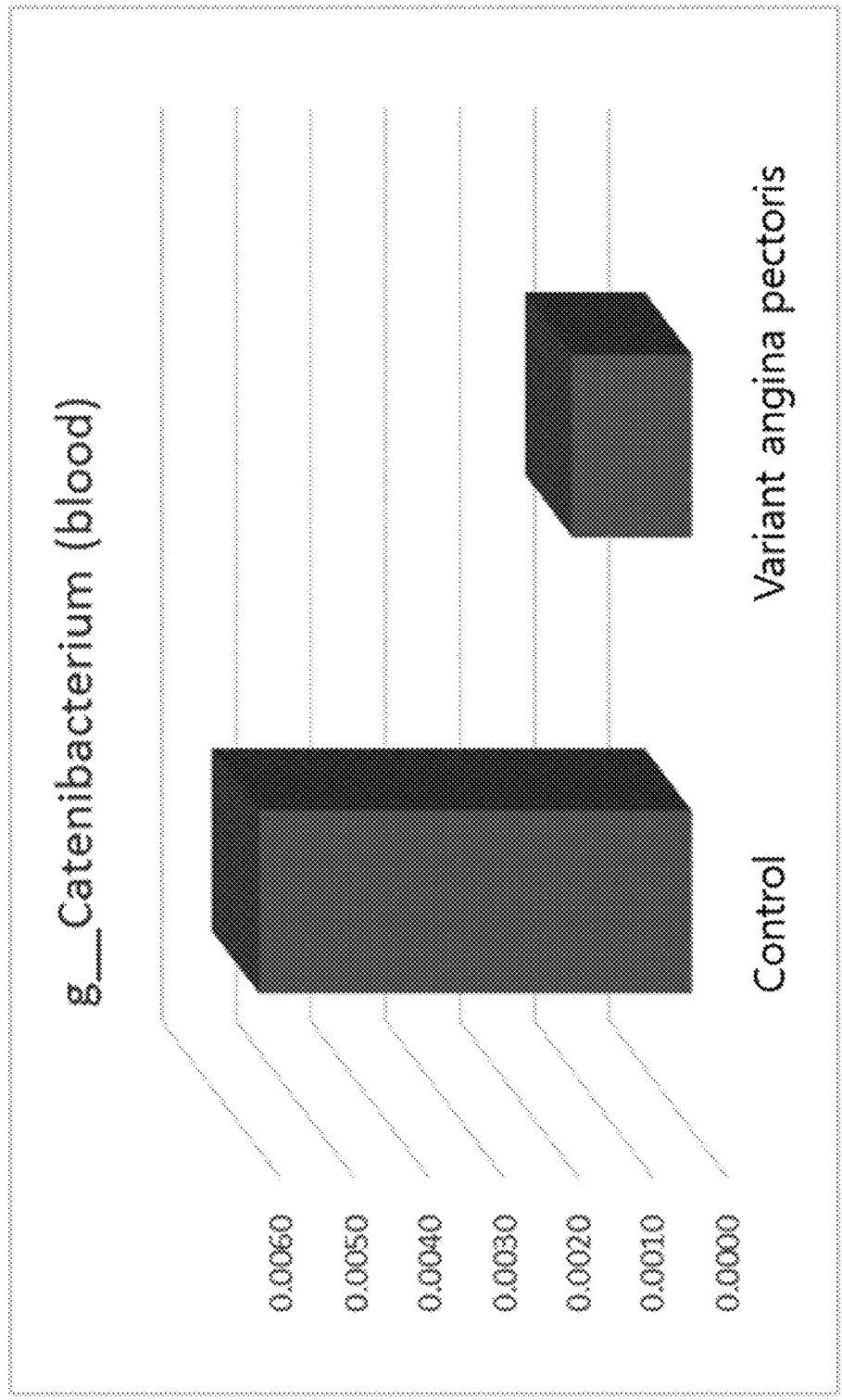
FIG. 10 is a result of comparing the distributions of vesicles derived from bacteria of the genus *Catenibacterium* after metagenomic analysis of bacteria-derived vesicles present in the blood of variant angina pectoris patients and a normal individual.

Example 11. Metagenomic Analysis of Bacteria-Derived Vesicles in Blood of Patient with Variant Angina Pectoris After a metagenomic analysis was performed using the method of Example 2 on the blood from 80 patients with variant angina pectoris, and 80 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with variant angina pectoris as compared to the blood from the normal individuals (see Table 11 and FIG. 10).

TABLE 11

| Blood | Control | | Variant angina pectoris | | t-test | |
|---|---|---|---|---|---|---|
| Taxon | Mean | SD | Mean | SD | p-value | Ratio |
| g_Catenibacterium | 0.0058 | 0.0122 | 0.0016 | 0.0039 | 0.004 | 0.28 |

Figure 11:
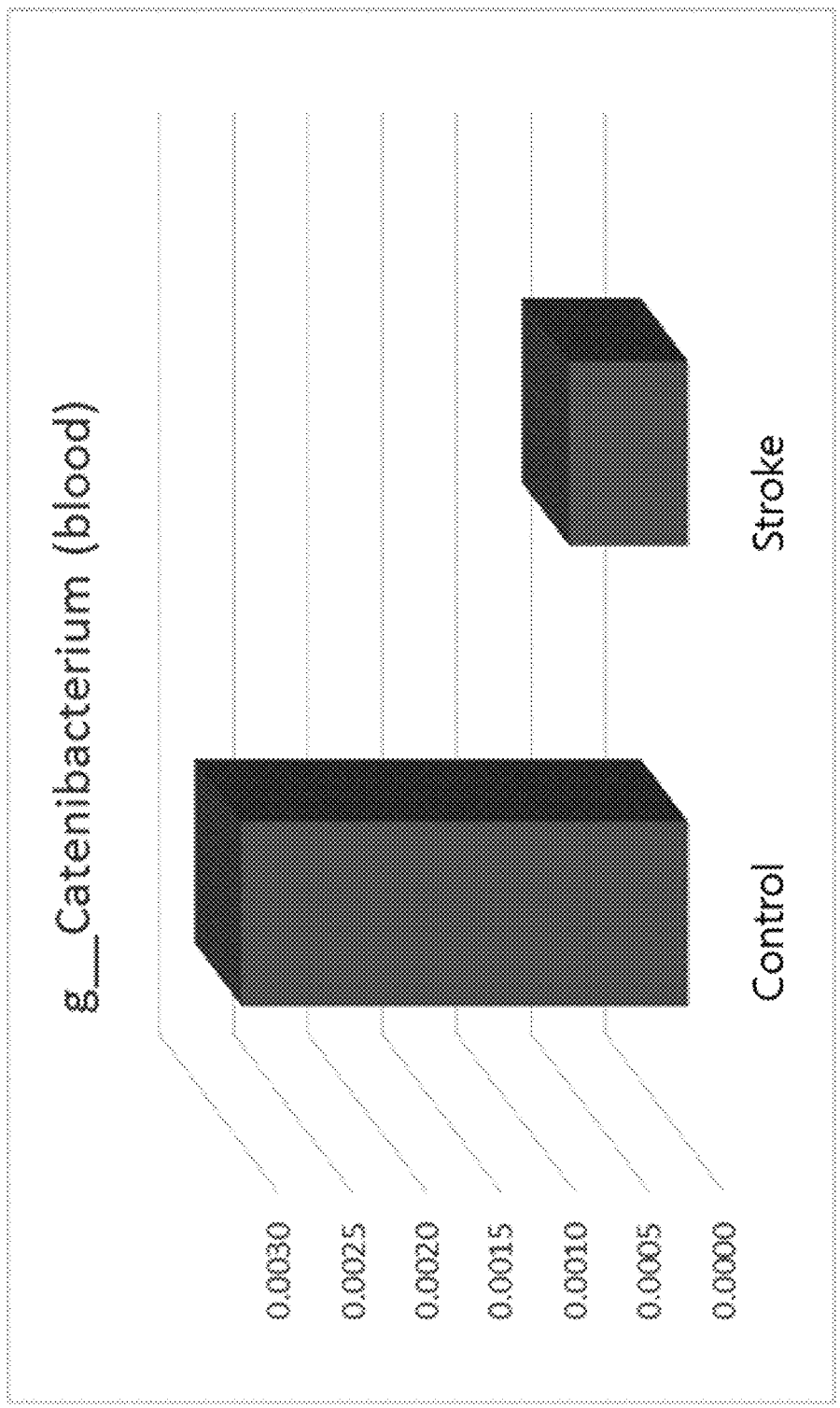
FIG. 11 is a result of comparing the distributions of vesicles derived from bacteria of the genus *Catenibacterium* after metagenomic analysis of bacteria-derived vesicles present in the blood of stroke patients and a normal individual.

Example 12. Metagenomic Analysis of Bacteria-Derived Vesicles in Blood of Patient with Stroke After a metagenomic analysis was performed using the method of Example 2 on the blood from 115 patients with stroke, and 109 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with stroke as compared to the blood from the normal individuals (see Table 12 and FIG. 11).

TABLE 12

| Blood | Control | | Stroke | | t-test | |
|---|---|---|---|---|---|---|
| Taxon | Mean | SD | Mean | SD | p-value | Ratio |
| g_Catenibacterium | 0.0030 | 0.0071 | 0.0008 | 0.0042 | 0.005 | 0.26 |

Figure 12:
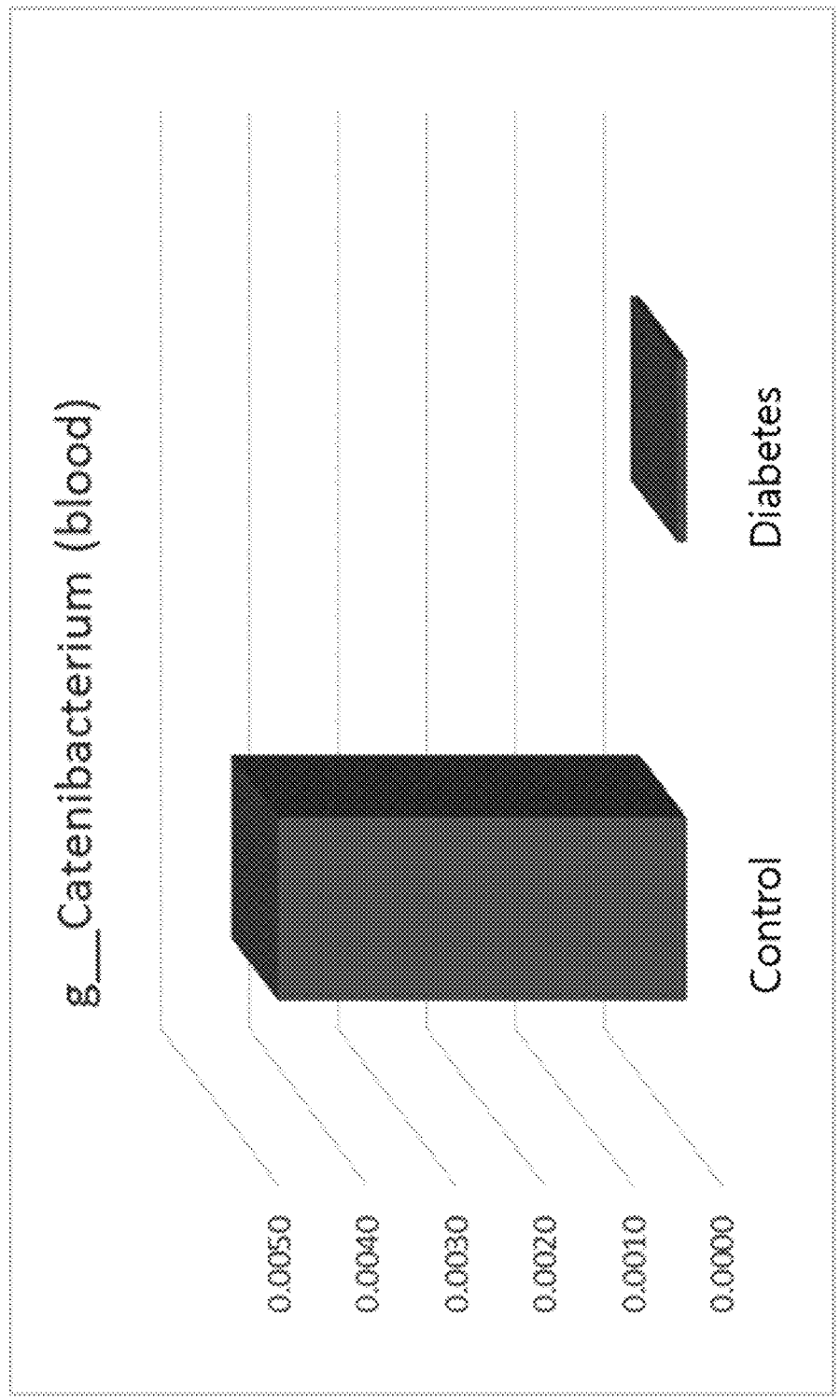
FIG. 12 is a result of comparing the distributions of vesicles derived from bacteria of the genus *Catenibacterium* after metagenomic analysis of bacteria-derived vesicles present in the blood of diabetes patients and a normal individual.

Example 13. Metagenomic Analysis of Bacteria-Derived Vesicles in Blood of Patient with Diabetes After a metagenomic analysis was performed using the method of Example 2 on the blood from 73 patients with diabetes, and 146 normal individuals who were matched in age and sex by extracting genes from vesicles present in the blood, the distribution of vesicles derived from bacteria of the genus *Catenibacterium* was evaluated. As a result, it was confirmed that vesicles derived from bacteria of the genus *Catenibacterium* were significantly decreased in the blood from the patients with diabetes as compared to the blood from the normal individuals (see Table 13 and FIG. 12).

TABLE 13

| Blood | Control | | Diabetes | | t-test | |
|---|---|---|---|---|---|---|
| Taxon | Mean | SD | Mean | SD | p-value | Ratio |
| g_Catenibacterium | 0.0046 | 0.0098 | 0.0001 | 0.0001 | <0.0001 | 0.03 |

Figure 13:
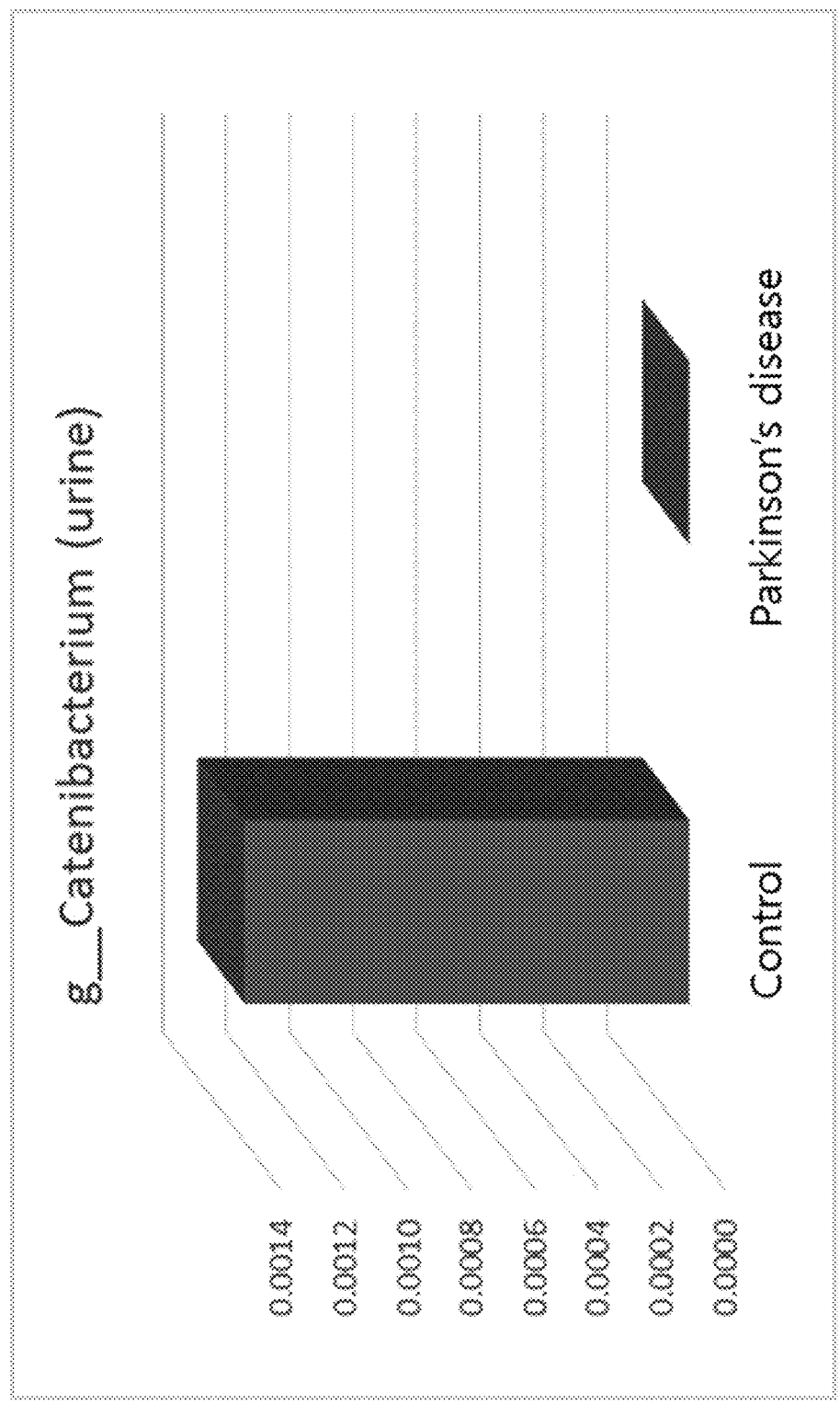
FIG. 13 is a result of comparing the distributions of vesicles derived from bacteria of the genus *Catenibacterium* after metagenomic analysis of bacteria-derived vesicles present in the urine of Parkinson's disease patients and a normal individual.

Example 14. Metagenomic Analysis of Bacteria-Derived Vesicles in Urine of Patient with Parkinson's Disease After a metagenomic analysis was performed using the method of Example 2 on the urine from 39 patients with Parkinson's disease, and 79 normal individuals who were matched in age and sex by extracting genes from vesicles present in the urine, the distribution of vesicles derived from bacteria of the genus *Catenibacterium* was evaluated. As a result, it was confirmed that vesicles derived from bacteria of the genus *Catenibacterium* were significantly decreased in the urine from the patients with Parkinson's disease as compared to the urine from the normal individuals (see Table 14 and FIG. 13).

TABLE 14

| Urine | Control | | Parkinson's disease | | t-test | |
|---|---|---|---|---|---|---|
| Taxon | Mean | SD | Mean | SD | p-value | Ratio |
| g_Catenibacterium | 0.0014 | 0.0036 | 0.0000 | 0.0000 | 0.01 | 0.00 |

Figure 14:
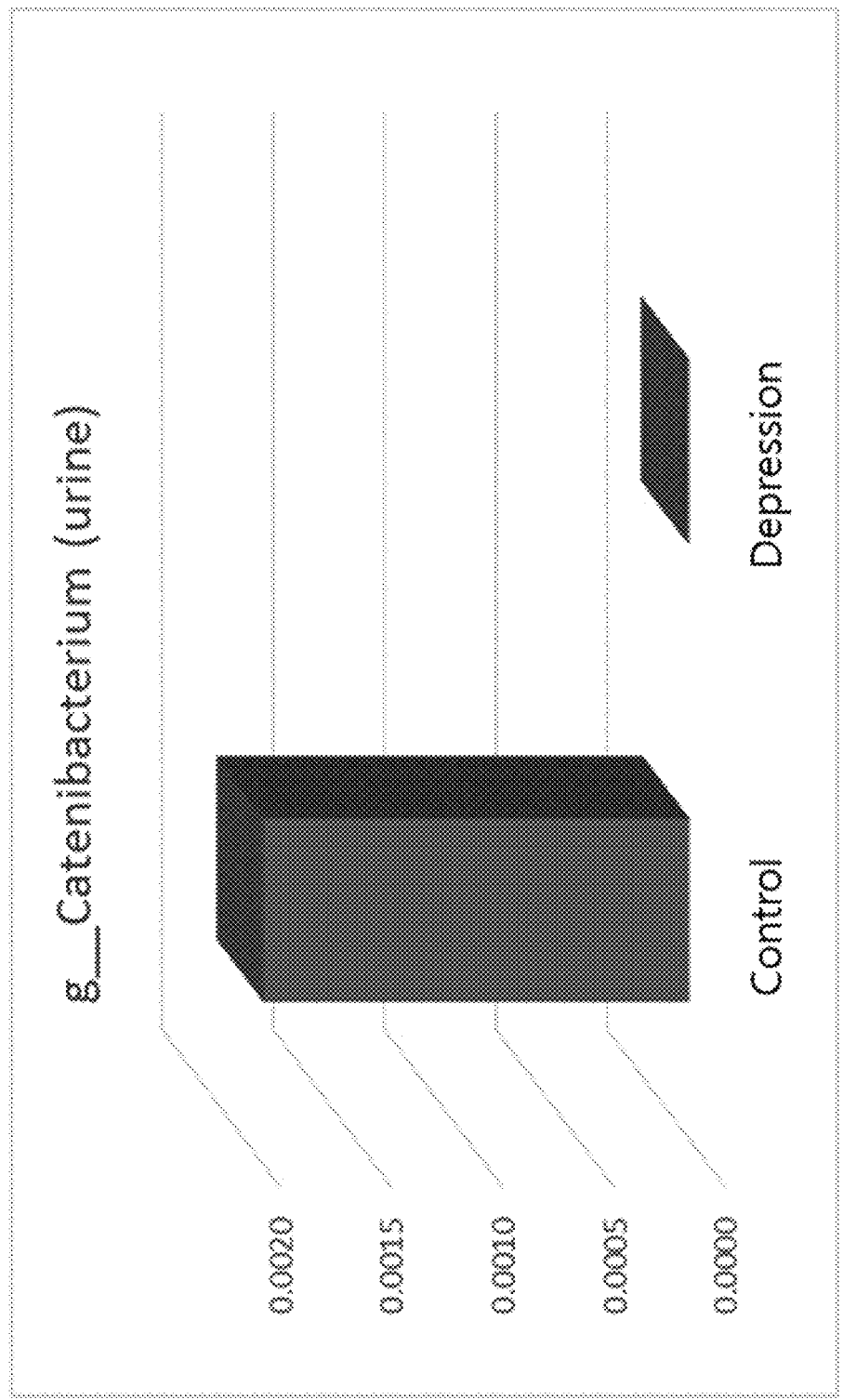
FIG. 14 is a result of comparing the distributions of vesicles derived from bacteria of the genus *Catenibacterium* after metagenomic analysis of bacteria-derived vesicles present in the urine of depression patients and a normal individual.

Example 15. Metagenomic Analysis of Bacteria-Derived Vesicles in Urine of Patient with Depression After a metagenomic analysis was performed using the method of Example 2 on the urine from 20 patients with depression, and 20 normal individuals who were matched in age and sex by extracting genes from vesicles present in the urine, the distribution of vesicles derived from bacteria of the genus *Catenibacterium* was evaluated. As a result, it was confirmed that vesicles derived from bacteria of the genus Catenibacterium were significantly decreased in the urine from the patients with depression as compared to the urine from the normal individuals (see Table 15 and FIG. 14).

TABLE 15

| Urine | Control | | Depression | | t-test | |
|---|---|---|---|---|---|---|
| Taxon | Mean | SD | Mean | SD | p-value | Ratio |
| g_Catenibacterium | 0.0019 | 0.0043 | 0.0000 | 0.0000 | 0.04 | 0.00 |

Example 16. Anti-Inflammatory Effects of Catenibacterium mituokai-Derived Vesicles Based on the results of the above examples, a *Catenibacterium mituokai* strain was cultured, and then vesicles thereof were isolated. The *Catenibacterium mituokai* strain was cultured in a brain heart infusion (BHI) medium until absorbance ($OD_{600}$) reached 1.0 to 1.5 in a 37° C. anaerobic chamber, and then sub-cultured. Afterward, a medium supernatant which does not contain the strain was collected, centrifuged at 10,000 g and 4° C. for 15 minutes, and filtered through a 0.45-μm filter. A supernatant obtained thereby was concentrated to a volume of 200 mL through ultrafiltration using a QuixStand benchtop system (GE Healthcare, UK) as a 100 kDa hollow filter membrane. Subsequently, the concentrated supernatant was filtered once again with a 0.22-μm filter and ultracentrifuged at 150,000 g and 4° C. for 3 hours, followed by suspension of a pellet in DPBS. Afterward, density gradient centrifugation was performed using 10%, 40% and 50% OptiPrep solutions (Axis-Shield PoC AS, Norway), and to prepare low-density solutions, the OptiPrep solutions were diluted with HEPES-buffered saline (20 mM HEPES, 150 mM NaCl, pH 7.4) before use. After centrifugation for 2 hours under conditions of 200,000 g and 4° C., each solution fractionated with an equal volume of 1 mL from the top layer was additionally ultracentrifuged for 3 hours under conditions of 150,000 g and 4° C. Afterward, a protein was quantified using a bicinchoninic acid (BCA) assay, and an experiment was performed on vesicles obtained as described above.

Figure 15:
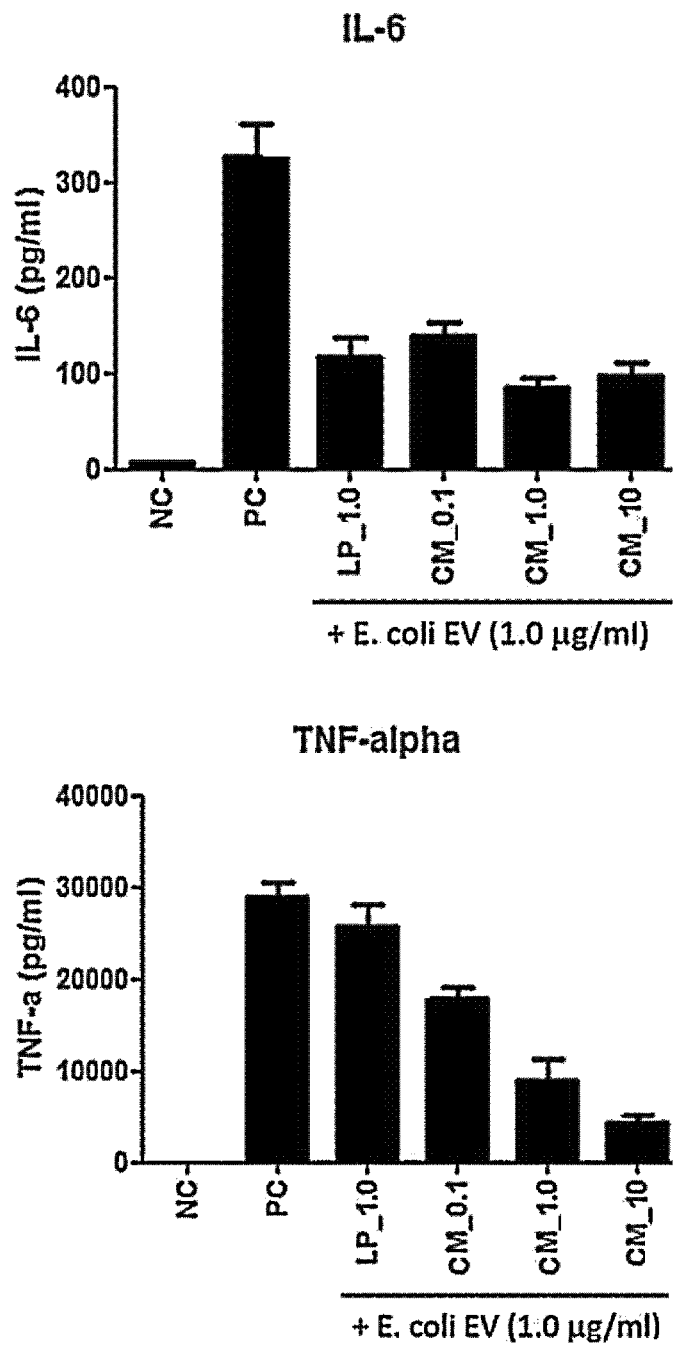
FIG. 15 is a result of evaluating an effect on the secretion of IL-6 and TNF-α which inflammatory mediators caused by *E. coli* EVs by pretreating bacteria of the genus *Catenibacterium*-derived vesicles before treatment of pathogenic vesicles such as *E. coli* EVs to evaluate anti-inflammatory and immunomodulatory effects of *Catenibacterium mituokai*-derived vesicles (NC: negative control; PC: positive control, *E. coli* EV 1 μg/ml; LP_1.0: *Lactobacillus plantarum* EV 1.0 μg/ml; GS_0.1, 1.0, 10: CM: *Catenibacterium mituokai* EV 0.1, 1.0, 10 μg/ml).

To examine the effect of the *Catenibacterium mituokai*-derived vesicles on the secretion of inflammatory mediators from inflammatory cells, a mouse macrophage cell line, Raw 264.7 cells, was treated with *Catenibacterium mituokai*-derived vesicles (*C. mituokai* EV) at various concentrations (0.1, 1, 10 μg/mL), and secretion amounts of inflammatory mediators (IL-6 and TNF-α) were measured by treating vesicles derived from *Escherichia coli* (*E. coli* EV) which are vesicles for inflammatory disease pathogenesis. More specifically, the Raw 264.7 cells were seeded in a 24-well cell culture plate at $1\times10^5$ per well, and incubated in DMEM for 24 hours. Afterward, a culture supernatant was collected in a 1.5 mL tube, centrifuged at 3000 g for 5 minutes, thereby collecting a supernatant. The supernatant was stored at 4° C., followed by ELISA. As a result, when *Catenibacterium mituokai*-derived vesicles were pretreated, it was confirmed that the secretion of the IL-6 and TNF-α by *E. coli* EVs was significantly suppressed (see FIG. 15). This result shows that inflammatory responses induced by pathogenic vesicles such as *E. coli*-derived vesicles can be effectively inhibited by the *Catenibacterium mituokai*-derived vesicles.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

Since vesicles derived from bacteria of the genus *Catenibacterium* according to the present invention may be used in a method of diagnosing a malignant disease such as colon cancer, pancreatic cancer, cholangiocarcinoma, ovarian cancer, bladder cancer or lymphoma, a cardiovascular disease such as myocardial infarction, atrial fibrillation, variant angina or stroke, diabetes, Parkinson's disease, and depression, and a composition for preventing, alleviating or treating the disease, they are expected to be effectively used in related medical and food industry fields.

What is claimed is:

1. A method of alleviating, inhibiting or treating inflammation, the method comprising administering to a subject in need thereof a composition consisting of an effective amount of an active ingredient in a pharmaceutically acceptable carrier, wherein the active ingredient is vesicles obtained from *Catenibacterium mitsuokai*, and wherein bacterial cells of *Catenibacterium mitsuokai* are removed from the composition.

2. The method of claim 1, wherein the vesicles have an average diameter of 10 to 200 nm.

3. The method of claim 1, wherein the composition is a pharmaceutical composition or a food composition.

4. The method of claim 1, wherein the vesicles are secreted naturally or artificially from *Catenibacterium mitsoukai*.

5. The method of claim 1, wherein the vesicles inhibit secretion of IL-6 or TNF-α and thereby inhibit the inflammation.

\* \* \* \* \*

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: 16S_V3_F
<220> FEATURE:
<221> NAME/KEY: misc_feature
<222> LOCATION: (42)..(42)
<223> OTHER INFORMATION: n is a, c, g, or t

<400> SEQUENCE: 1
tcgtcggcag cgtcagatgt gtataagaga cagcctacgg gnggcwgcag            50

<210> SEQ ID NO 2
<211> LENGTH: 55
<212> TYPE: DNA
<213> ORGANISM: Artificial Sequence
<220> FEATURE:
```

| | |
|---|---|
| <223> OTHER INFORMATION: 16S_V4_R | |
| <400> SEQUENCE: 2 | |
| gtctcgtggg ctcggagatg tgtataagag acaggactac hvgggtatct aatcc | 55 |